(12) United States Patent
Boles

(10) Patent No.: US 11,867,661 B2
(45) Date of Patent: Jan. 9, 2024

(54) SYSTEMS AND METHODS FOR DETECTION OF GENETIC STRUCTURAL VARIATION USING INTEGRATED ELECTROPHORETIC DNA PURIFICATION

(71) Applicant: Sage Science, Inc., Beverly, MA (US)

(72) Inventor: T. Christian Boles, Bedford, MA (US)

(73) Assignee: SAGE SCIENCE, INC., Beverly, MA (US)

( * ) Notice: Subject to any disclaimer, the term of this patent is extended or adjusted under 35 U.S.C. 154(b) by 234 days.

(21) Appl. No.: 16/603,573

(22) PCT Filed: Apr. 6, 2018

(86) PCT No.: PCT/US2018/026603
§ 371 (c)(1),
(2) Date: Oct. 7, 2019

(87) PCT Pub. No.: WO2018/187779
PCT Pub. Date: Oct. 11, 2018

(65) Prior Publication Data
US 2021/0088473 A1    Mar. 25, 2021

Related U.S. Application Data

(60) Provisional application No. 62/483,261, filed on Apr. 7, 2017.

(51) Int. Cl.
*G01N 27/447* (2006.01)
*C12Q 1/6806* (2018.01)
(Continued)

(52) U.S. Cl.
CPC ....... *G01N 27/4473* (2013.01); *C12Q 1/6806* (2013.01); *C12Q 1/686* (2013.01); *G01N 27/44739* (2013.01); *G01N 27/453* (2013.01)

(58) Field of Classification Search
CPC ......... G01N 27/4473; G01N 27/44739; G01N 27/453; G01N 27/44791; C12Q 1/6806; C12Q 1/686
See application file for complete search history.

(56) References Cited

U.S. PATENT DOCUMENTS 3,407,133 A   10/1968 Oliva et al.
3,533,933 A   10/1970 Strauch et al.
(Continued)

FOREIGN PATENT DOCUMENTS

CN   101024851 A   8/2007
CN   101907532 A   12/2010
(Continued)

OTHER PUBLICATIONS

Search Report and Written Opinion for International Application No. PCT/US2018/026603, dated Aug. 1, 2018.
(Continued)

*Primary Examiner* — Alexander S Noguerola
(74) *Attorney, Agent, or Firm* — COOLEY LLP

(57) ABSTRACT

An electrophoresis cassette may include sample well(s), gel column(s) containing a separation gel, and elution modules arranged adjacent the gel column(s). A sample may be provided to the electrophoresis cassette and high-molecular weight (HMW) DNA may be isolated from the sample. Single-copy DNA sequences may be cleaved on both sides of a repeat region of the DNA sequences to produce a cleaved sample, which then may be fractionated using gel electrophoresis. DNA fractions may be isolated from consecutive sections of the separation gel and subjected to PCR assays to detect single-copy sequences within the DNA fraction, said single-copy sequence containing repeat expansion sequences. The subjected DNA fractions may be electroeluted into the plurality of elution modules. A size of DNA fractions having the repeat expansion sequences may
(Continued)

be determined. It is also determined if that size is above a normal repeat size range.

7 Claims, 15 Drawing Sheets

Specification includes a Sequence Listing.

(51) Int. Cl.
*C12Q 1/686* (2018.01)
*G01N 27/453* (2006.01)

(56) References Cited

U.S. PATENT DOCUMENTS

| | | | |
|---|---|---|---|
| 3,616,454 | A | 10/1971 | Levy et al. |
| 3,980,546 | A | 9/1976 | Caccavo |
| 4,175,662 | A | 11/1979 | Zold |
| 4,315,812 | A | 2/1982 | Karlson |
| 4,375,401 | A | 3/1983 | Catsimpoolas |
| 4,545,888 | A | 10/1985 | Walsh |
| 4,608,147 | A | 8/1986 | Clad |
| 4,655,898 | A | 4/1987 | Poulhes et al. |
| 4,695,548 | A | 9/1987 | Cantor et al. |
| 4,707,233 | A | 11/1987 | Margolis |
| 4,708,782 | A | 11/1987 | Andresen et al. |
| 4,834,862 | A | 5/1989 | Breiner et al. |
| 4,835,263 | A | 5/1989 | Nguyen et al. |
| 4,900,677 | A | 2/1990 | Hewitt |
| 4,948,481 | A | 8/1990 | Mullner |
| 4,954,444 | A | 9/1990 | Eveleigh et al. |
| 5,062,942 | A | 11/1991 | Kambara et al. |
| 5,169,511 | A | 12/1992 | Allington et al. |
| 5,217,591 | A | 6/1993 | Gombocz et al. |
| 5,242,568 | A | 9/1993 | Ehr et al. |
| 5,273,881 | A | 12/1993 | Sena et al. |
| 5,304,487 | A | 4/1994 | Wilding et al. |
| 5,384,022 | A | 1/1995 | Rajasekaran |
| 5,433,837 | A | 7/1995 | Brunk et al. |
| 5,443,704 | A | 8/1995 | Kirkpatrick et al. |
| 5,457,050 | A | 10/1995 | Mazurek |
| 5,460,941 | A | 10/1995 | Camerini-Otero et al. |
| 5,482,836 | A | 1/1996 | Cantor et al. |
| 5,538,614 | A | 7/1996 | Han |
| 5,707,812 | A | 1/1998 | Horn et al. |
| 5,717,602 | A | 2/1998 | Kenning |
| 5,800,690 | A | 9/1998 | Chow et al. |
| 5,801,115 | A | 9/1998 | Albers et al. |
| 5,804,684 | A | 9/1998 | Su |
| 5,804,864 | A | 9/1998 | Akiyama |
| 5,827,418 | A | 10/1998 | Haven et al. |
| 5,840,169 | A | 11/1998 | Andersen |
| 5,929,208 | A | 7/1999 | Heller et al. |
| 6,290,831 | B1 | 9/2001 | Liran et al. |
| 6,306,348 | B1 | 10/2001 | Havens et al. |
| 6,319,472 | B1 | 11/2001 | Ackley et al. |
| 6,334,164 | B1 | 12/2001 | Okazawa et al. |
| 6,344,325 | B1 | 2/2002 | Quake et al. |
| 6,366,924 | B1 | 4/2002 | Parce |
| 6,369,893 | B1 | 4/2002 | Christel et al. |
| 6,388,746 | B1 | 5/2002 | Eriksson et al. |
| 6,430,512 | B1 | 8/2002 | Gallagher |
| 6,541,226 | B1 | 4/2003 | Shigemori et al. |
| 6,611,768 | B2 | 8/2003 | Gallagher |
| 6,718,742 | B1 | 4/2004 | Baker |
| 6,808,609 | B1 | 10/2004 | Soane et al. |
| 6,834,240 | B2 | 12/2004 | Gallagher |
| 6,867,851 | B2 | 3/2005 | Blumenfeld et al. |
| 6,887,668 | B2 | 5/2005 | Liu et al. |
| 6,914,137 | B2 | 7/2005 | Baker |
| 6,919,571 | B2 | 7/2005 | Lai et al. |
| 6,964,736 | B2 | 11/2005 | Quake et al. |
| 7,056,746 | B2 | 6/2006 | Seul et al. |
| 7,108,775 | B2 | 9/2006 | Bahatt et al. |
| 7,122,104 | B2 | 10/2006 | Cabilly et al. |
| 7,150,812 | B2 | 12/2006 | Huang et al. |
| 7,198,703 | B2 | 4/2007 | Rooney et al. |
| 7,413,642 | B2 | 8/2008 | Hassard et al. |
| 7,419,784 | B2 | 9/2008 | Dubrow et al. |
| 7,735,652 | B2 | 6/2010 | Inglis et al. |
| 7,988,840 | B2 | 8/2011 | Huang et al. |
| 8,361,298 | B2 | 1/2013 | Sabin et al. |
| 8,361,299 | B2 | 1/2013 | Sabin et al. |
| 9,012,373 | B2 | 4/2015 | Boles et al. |
| 9,599,590 | B2 | 3/2017 | Sabin et al. |
| 9,663,779 | B2 | 5/2017 | Fabis et al. |
| 9,719,961 | B2 | 8/2017 | Sabin et al. |
| 10,131,901 | B2 | 11/2018 | Abrams et al. |
| 10,473,619 | B2 | 11/2019 | Sabin et al. |
| 10,738,298 | B2 | 8/2020 | Abrams et al. |
| 11,542,495 | B2 | 1/2023 | Mitra et al. |
| 2001/0000103 | A1 | 4/2001 | Rhodes et al. |
| 2002/0076825 | A1 | 6/2002 | Cheng et al. |
| 2002/0170831 | A1 | 11/2002 | Roeth et al. |
| 2002/0187503 | A1 | 12/2002 | Harrold et al. |
| 2003/0151735 | A1 | 8/2003 | Blumenfeld et al. |
| 2003/0170609 | A1 | 9/2003 | Rigler |
| 2003/0190634 | A1 | 10/2003 | Barany et al. |
| 2004/0011650 | A1 | 1/2004 | Zenhausern et al. |
| 2004/0089546 | A1 | 5/2004 | Bahatt et al. |
| 2004/0144651 | A1 | 7/2004 | Huang et al. |
| 2005/0205427 | A1 | 9/2005 | Boschetti et al. |
| 2006/0154247 | A1 | 7/2006 | Baker et al. |
| 2006/0193752 | A1 | 8/2006 | Levine |
| 2006/0223178 | A1 | 10/2006 | Barber et al. |
| 2007/0284250 | A1 | 12/2007 | Magnant et al. |
| 2007/0286773 | A1 | 12/2007 | Schlautmann et al. |
| 2008/0023399 | A1 | 1/2008 | Inglis et al. |
| 2008/0057557 | A1 | 3/2008 | Margalit |
| 2008/0138809 | A1 | 6/2008 | Kapur et al. |
| 2009/0241216 | A1 | 9/2009 | Wang-Pruski et al. |
| 2009/0308749 | A1 | 12/2009 | Park |
| 2010/0048412 | A1 | 2/2010 | Liu et al. |
| 2010/0059414 | A1 | 3/2010 | Sturm et al. |
| 2010/0126862 | A1 | 5/2010 | Sabin et al. |
| 2010/0233693 | A1 | 9/2010 | Kopf-Sill et al. |
| 2011/0062024 | A1 | 3/2011 | Sabin et al. |
| 2011/0114487 | A1 | 5/2011 | Schmidt et al. |
| 2011/0287436 | A1 | 11/2011 | Shannon et al. |
| 2012/0195809 | A1 | 8/2012 | Polwart et al. |
| 2013/0020199 | A1 | 1/2013 | Margalit |
| 2013/0079251 | A1 | 3/2013 | Boles |
| 2013/0217022 | A1 | 8/2013 | Cao et al. |
| 2013/0233714 | A1 | 9/2013 | Sabin et al. |
| 2013/0240360 | A1 | 9/2013 | Sabin et al. |
| 2014/0038241 | A1 | 2/2014 | Zhou et al. |
| 2014/0127752 | A1 | 5/2014 | Zhou et al. |
| 2014/0271602 | A1 | 9/2014 | Zhang et al. |
| 2014/0284213 | A1 | 9/2014 | Sabin et al. |
| 2014/0356867 | A1 | 12/2014 | Peter et al. |
| 2015/0027891 | A1 | 1/2015 | Puleo et al. |
| 2015/0101932 | A1* | 4/2015 | Sabin ............... G01N 27/44739 204/627 |
| 2015/0166986 | A1 | 6/2015 | Boles et al. |
| 2016/0115536 | A1 | 4/2016 | Mead et al. |
| 2016/0370318 | A1 | 12/2016 | Sabin et al. |
| 2017/0239658 | A1 | 8/2017 | Abrams et al. |
| 2017/0240882 | A1 | 8/2017 | Abrams et al. |
| 2017/0254774 | A1 | 9/2017 | Sabin et al. |
| 2020/0041449 | A1 | 2/2020 | Abrams et al. |
| 2021/0062180 | A1 | 3/2021 | Abrams et al. |
| 2021/0207122 | A1 | 7/2021 | Mitra et al. |
| 2023/0167430 | A1 | 6/2023 | Boles |

FOREIGN PATENT DOCUMENTS

| | | |
|---|---|---|
| CN | 102268426 A | 12/2011 |
| CN | 102305823 A | 1/2012 |
| CN | 103122381 A | 5/2013 |
| CN | 104968784 A | 10/2015 |
| CN | 105408497 A | 3/2016 |
| DE | 102004025650 A1 | 6/2006 |
| EP | 0334615 A2 | 9/1989 |
| EP | 0382426 A2 | 8/1990 |

(56) References Cited

FOREIGN PATENT DOCUMENTS

| | | |
|---|---|---|
| EP | 1354952 A1 | 10/2003 |
| EP | 1384067 B1 | 7/2007 |
| GB | 2148325 A | 5/1985 |
| GB | 2148326 A | 5/1985 |
| JP | S62239047 A | 10/1987 |
| JP | S6322254 B2 | 5/1988 |
| JP | H07198680 A | 8/1995 |
| JP | 2000224980 A | 8/2000 |
| JP | 2002518672 A | 6/2002 |
| JP | 2002310992 A | 10/2002 |
| JP | 2002323477 A | 11/2002 |
| JP | 2004510170 A | 4/2004 |
| JP | 2005147957 A | 6/2005 |
| JP | 2005532545 A | 10/2005 |
| WO | WO-8606743 A1 | 11/1986 |
| WO | WO-9604000 A1 | 2/1996 |
| WO | WO-9623213 A1 | 8/1996 |
| WO | WO-9810277 A1 | 3/1998 |
| WO | WO-0228516 A1 | 4/2002 |
| WO | WO-0244706 A1 | 6/2002 |
| WO | WO-03087370 A1 | 10/2003 |
| WO | WO-2005093388 A1 | 10/2005 |
| WO | WO-2006031385 A2 | 3/2006 |
| WO | WO-2006108101 A2 | 10/2006 |
| WO | WO-2008016414 A2 | 2/2008 |
| WO | WO-2008041718 A1 | 4/2008 |
| WO | WO-2010042766 A1 | 4/2010 |
| WO | WO-2010048605 A1 | 4/2010 |
| WO | WO-2012021803 A1 | 2/2012 |
| WO | WO-2012171329 A1 | 12/2012 |
| WO | WO-2013020089 A2 | 2/2013 |
| WO | WO-2014020137 A1 | 2/2014 |
| WO | WO-2014059188 A1 | 4/2014 |
| WO | WO-2014065596 A1 | 5/2014 |
| WO | WO-2014186819 A1 | 11/2014 |
| WO | WO-2015040075 A1 | 3/2015 |
| WO | WO-2016014409 A1 | 1/2016 |
| WO | WO-2016061416 A1 | 4/2016 |
| WO | WO-2016061556 A1 | 4/2016 |
| WO | WO-2016100955 A2 | 6/2016 |
| WO | 2017/040813 A2 | 3/2017 |
| WO | WO-2017087979 A1 | 5/2017 |
| WO | WO-2017139669 A1 | 8/2017 |
| WO | WO-2018067736 A1 | 4/2018 |
| WO | WO-2018187779 A1 | 10/2018 |
| WO | WO-2019136301 A1 | 7/2019 |
| WO | WO-2021217052 A1 | 10/2021 |

OTHER PUBLICATIONS

ABI PRISM™ 377: DNA Sequencer. Perkin Elmer User's Manual, Part No. 903433, Rev. A., 1995, 4-58-5-17, 1-12.
Adey, et al. "In vitro, long-range sequence information for de novo genome assembly via transposase contiguity." Genome Research, 2014, 24(12):2041-2049.
Amini, et al. "Haplotype-resolved whole genome sequencing by contiguity preserving transposition and combinatorial indexing." Nature Genetics, Dec. 2014, 46(12):1343-1349.
Ansorge, et al. "Field gradients improve resolution on DNA sequencing gels." Journal of Biochemical and Biophysical Methods, 1984, 10:237-243.
Antunes, et al. "Targeted DNA excision in Arabidopsis by a re-engineered homing endonuclease." BMC Biotechnology, 2012, 12(86):1-12.
Australian Patent Examination Report No. 1 corresponding to Australian Application No. 2013329110, dated Jul. 28, 2016, 3 pages.
Bakajin, et al. "Separation of 100-kilobase DNA molecules in 10 seconds." Anal. Chem., 2001, 73(24):6053-6056.
Bibin, et al. "Depletion effects in binary hard-sphere fluids." J. Phys.: Condens. Matter, 1996, 8(50):10799-10821.
Bogdanove and Voytas "TAL effectors: customizable proteins for DNA targeting." Science, Sep. 30, 2011, 333:1843-1846.
Boncinelli et al. "An agarose gel resolving a wide range of DNA fragment lengths." Anal. Biochem., 1983, 134:40-43.
Boom, et al. "Rapid and Simple Method for Purification of Nucleic Acids." Journal of Clinical Microbiology, Mar. 1990, 28(3):495-503.
Börgstrom, et al. "Large Scale Library Generation for High Throughput Sequencing." PLoS One, Apr. 27, 2011, 6(4):e19119:1-6.
Chan, et al. "DNA kinetics in microfabricated devices." Micro Electro Mechanical Systems, 2002, 60-63.
Chang, et al. "A New Mass-Spectrometry-compatible Degradable Surfactant for Tissue Proteomics." J. Proteome Res., Mar. 6, 2015, 14(3):1587-1599.
Chen, et al. "An inexpensive microslab gel DNA electrophoresis system with real-time fluorescence detection." Electrophoresis, 2006, 27(2):387-393.
Cheng, et al. "Interaction between DNA and Trimethyl-Ammonium Bromides with Different Alkyl Chain Lengths." The Scientific World Journal, Jan. 16, 2014, 2014(863409):1-9.
Chiu, et al. "Differential Dependence on Chromatin Structure for Copper and Iron Ion Induction of DNA Double-Strand Breaks." Biochemistry, 1995, 34:2653-2661.
Ciulla, et al. "A Simple Method for DNA Purification from Peripheral Blood." Analytical Biochemistry, 1988, 174:485-488.
Cong, et al. "Multiplex Genome Engineering Using CRISPR/Cas Systems." Science Feb. 15, 2013, 339:819-823.
Cost, et al. "Directed assembly of DNA molecules via simultaneous ligation and digestion." BioTechniques, 2007, 42(1):84-89.
Costa, et al. "Isolation of proteins and nucleic acids by electrophoresis on disposable gel columns." Electrophoresis, 1996, 17(4):781-783.
Cunha, et al. "Polymer-Mediated Compaction and Internal Dynamics of Isolated *Escherichia coli* Nucleoids." J. Struct. Biol., 2001, 136(1):53-66.
Davis, et al. "Deterministic hydrodynamics: taking blood apart." PNAS, Oct. 3, 2006, 103(40):14779-14784.
Diehl, et al. "BEAMing: single-molecule PCR on microparticles in water-in-oil emulsions." Nat. Methods., Jul. 2006, 3(7):551-559.
DNA Analysis, The Development of a Portable High-Speed DNA Analysis DevicePaving the Way Towards Point-of-Care Diagnosis and Advanced Medical Treatment, http://www.azonano.com/Details.asp7Article ID=1783, 2006, 6 pages.
Duke, "Monte Carlo reptation model of gel electrophoresis: Steady state behavior." J. Chem. Phys. Dec. 15, 1990, 93(12):9049-9054.
Duyster, et al. "Translocations involving anaplastic lymphoma kinase (ALK)." Oncogene, 2001, 20(40):5623-5637.
Eckhardt, "A rapid method for the identification of plasmid desoxyribonucleic acid in bacteria." Plasmid, 1978, 1(4):584-588.
Esvelt, et al. "Genome-scale engineering for systems and synthetic biology." Mol Syst Biol. Jan. 22, 2013, 9(641):1-17.
Extended European Search Report for European Application No. 15851562.7, dated Jan. 29, 2018, 6 pages.
Extended European Search Report for European Application No. 16867354.9, dated Mar. 22, 2019, 9 pages.
Extended European Search Report for European Application No. 17859138.4, dated Apr. 15, 2020, 6 pages.
Full English language translation of Quan Du WO 2012/171329 A1, patent published Jun. 12, 2012, 54 pages.
Gardella, et al. "Detection of Circular and Linear Herpesvirus DNA Molecules in Mammalian Cells by Gel Electrophoresis." Journal of Virology, Apr. 1984, 50(1):248-254.
Gasiunas, et al. "Cas9-crRNA ribonucleoprotein complex mediates specific DNA cleavage for adaptive immunity in bacteria." PNAS, Sep. 4, 2012, 109(39):E2579-2586.
Girvitz, et al. "A Rapid and Efficient Procedure for the Purification of DNA from Agarose Gels." Analytical Biochemistry, 1980, 106(2):492-496.
Gnirke A., et al. "Solution Hybrid Selection with Ultra-Long Oligonucleotides For Massively Parallel Targeted Sequencing." Nature Biotechnolgy, Feb. 2009, 27(2):182-189 (24 pages total).
Goryshin, et al. "Tn5 in vitro Transposition." The Journal of Biological Chemistry, 1998, 273(13):7367-7374.
Green, et al. "Charting a Course for Genomic Medicine from Base Pairs to Bedside." Nature, Feb. 10, 2011, 470:204-213.

(56) References Cited

OTHER PUBLICATIONS

Griffin IV, et al. "In vitro Transposition of Tn552: A Tool for DNA Sequencing and Mutagenesis." Nucleic Acids Research, 1999, 27(19):3859-3865.
Hamzah, "The effect of viscoelastic fluids on flows generated by spherical objects during sedimentation." PhD thesis, Massachusetts Institute of Technology, 2012, 27 pages.
Hanemaaijer, et al. "Characterization of Clean and Fouled Ultrafiltration Membranes." Desalination, 1988, 68:93-108.
Heller, et al. "Microelectrophoresis for the separation of DNA fragments." Electrophoresis, 1992, 13(1):512-520.
Hoffman, et al., "Hydrogels for biomedical applications." Advanced Drug Discovery Reviews, 2012, 64:18-23.
Hogan and Austin, "Importance of DNA stiffness in protein-DNA binding specificity." Nature, Sep. 1987, 329(6136):263-266.
Holland, et al. "Isolation and Characterization of a Small Catalytic Domain Released from the Adenylate Cyclase from *Escherichia coli* by Digestion with Trypsin." The Journal of Biological Chemistry, Oct. 15, 1988, 263(29):14661-14668.
Hsu, et al. "Development and Applications of CRISPR-Cas9 for Genome Engineering." Cell, Jun. 5, 2014, 157(6):1262-1278.
Hsu, et al. "DNA targeting specificity of RNA-guided Cas9 nucleases." Nat Biotechnol., Sep. 2013, 31(9):827-832.
Huang, et al. "A DNA prism for high-speed continuous fractionation of large DNA molecules." Nature Biotechnology, Oct. 2002, 20(10):1048-1051.
Huang, et al. "Continuous Particle Separation Through Deterministic Lateral Displacement." Science, May 14, 2004, 304:987-990.
Hughes, et al. "Expression profiling using microarrays fabricated by an ink-jet oligonucleotide synthesizer." Nature Biotechnology, Apr. 2001,19(4):342-347.
Inglis, et al. "Critical particle size for fractionation by deterministic lateral displacement." Lab Chip, 2006, 6(5):655-658.
Inglis, et al. "Determining blood cell size using microfluidic hydrodynamics." J. Immunol. Methods, 2008, 329(1):151-156.
Inoue, et al. "I-shaped microchannel array chip for parallel electrophoretic analyses." Analytical Chemistry, 2007, 79:2168-2173.
International Preliminary Report on Patentability, dated Apr. 18, 2017, for International Application No. PCT/US2015/056104, 8 pages.
International Preliminary Report on Patentability, dated Apr. 9, 2019, for International Application No. PCT/US2017/055193, 8 pages.
International Preliminary Report on Patentability, dated Aug. 14, 2018, for International Application No. PCT/US2017/017508, 14 pages.
International Preliminary Report on Patentability, dated Jul. 7, 2020, for International Application No. PCT/US2019/012416, 7 pages.
International Preliminary Report on Patentability, dated May 22, 2018, for International Application No. PCT/US2016/063190, 8 pages.
International Preliminary Report on Patentability, dated Oct. 8, 2019, for International Application No. PCT/US2018/026603, 8 pages.
International Preliminary Report on Patentability for International Application No. PCT/US2009/060065, dated Dec. 7, 2010, 15 pages.
International Preliminary Report on Patentability for International Application No. PCT/US2012/049603, dated Feb. 4, 2014, 7 pages.
International Preliminary Report on Patentability for International Application No. PCT/US2013/064403, dated Apr. 14, 2015, 12 pages.
International Preliminary Report on Patentability for International Application No. PCT/US2015/055833, dated Apr. 18, 2017, 11 pages.
International Search Report and the Written Opinion for International Application No. PCT/US2013/064403, dated Jan. 24, 2014, 17 pages.
International Search Report and Written Opinion for International Application No. PCT/US2012/049603, dated May 17, 2013, 13 pages.
International Search Report and Written Opinion for International Application No. PCT/US2015/055833, dated Feb. 2, 2016, 14 pages.
International Search Report and Written Opinion, dated Dec. 11, 2017, for International Application No. PCT/US2017/055193, 9 pages.
International Search Report and Written Opinion, dated Feb. 8, 2010, for International Application No. PCT/US2009/060065, 12 pages.
International Search Report and Written Opinion, dated Feb. 12, 2016, for International Application No. PCT/US2015/056104, 11 pages.
International Search Report and Written Opinion, dated Feb. 3, 2017, for International Application No. PCT/US2016/063190, 10 pages.
International Search Report and Written Opinion, dated Jun. 27, 2017, for International Application No. PCT/US2017/017508, 20 pages.
International Search Report and Written Opinion, dated Mar. 7, 2019, for International Application No. PCT/US2019/012416, 14 pages.
Invitation to Pay Additional Fees, dated Apr. 3, 2017, for International Application No. PCT/US2017/017508, 4 pages.
Japanese Office Action dated Jun. 14, 2016, corresponding to Japanese Application No. 2014-524127, 7 pages.
Jinek, et al. "A Programmable Dual-RNA-Guided DNA Endonuclease in Adaptive Bacterial Immunity." Science, Aug. 17, 2012, 337(6096):816-821.
Johnson, et al. "Sizing of DNA fragments by flow cytometry." Proc. SPIE, 1993, 1895:69-78.
Kaabouch, et al. "An Analysis System for DNA Gel Electrophoresis Images Based on Automatic Thresholding an Enhancement", Electro/Information Technology, 2007 IEEE International Conference on May 17-20, 2007, 26-31.
Karvelis, et al. "Programmable DNA cleavage in vitro by Cas9." Biochem. Soc. Trans., 2013, 41(6):1401-1406.
Khandurina, et al. "Micropreparative Fraction Collection in Microfluidic Devices." Anal. Chem., 2002, 74(7):1737-1740.
Kumar, et al. "Pyrrolidine Nucleic Acids: DNA/PNA Oligomers with 2-Hydroxy/Aminomethyl-4(thymin-1-yl)pyrrolidine-N-acetic acid." Organic Letters, 2001, 3(9):1269-1272.
Kunkel, et al. "Analysis of Human Y-Chromosome-Specific Reiterated DNA in Chromosome Variants." PNAS USA, Mar. 1977, 74(3):1245-1249.
La Spada and Taylor, "Repeat expansion disease: Progress and puzzles in disease pathogenesis." Nature Reviews Genetics, Apr. 2010, 11(4):247-258.
Laemmli, "Cleavage of structural proteins during the assembly of the head of bacteriophage T4." Nature, Aug. 15, 1970, 227:680-685.
Lagriffoul, et al. "The Synthesis, Co-Oligomerization and Hybridization of a Thymine-Thymine Heterodimer Containing PNA", Bioorganicand Medical Chemistry Letters, 1994, 4(8):1081-1082.
Lam, et al. "Genome mapping on nanochamlel arrays for structural variation analysis and sequence assembly." Nat. Biotechnol., Aug. 2012, 30(8):771-776.
Ledford, "AstraZeneca launches project to sequence 2 million genomes." Nature: International Weekly Journal of Science, 2016, 532(7600):427, 4 pages.
Lee and Krell, "Generation and Analysis of Defective Genomes of *Autographa califomica* Nuclear Polyhedrosis Virus." Journal of Virology, Jul. 1992, 66(7):4339-4347.
Lerman, et al. "A Transition to a Compact Form of DNA in Polymer Solutions." PNAS USA, Aug. 1971,68(8): 1886-1890.
Li, et al. "A simultaneous space sampling method for DNA fraction collection using a comb structure in microfluidic devices." Electrophoresis, 2011, 32(23):3392-3398.
Li, et al. "Design of a PMMA Chip for Selective Extraction of Size-Fractioned DNA." Proceedings of the 1st IEEE International Conference on Nano/Micro Engineered and Molecular Systems, Zhuhai China, Jan. 18-21, 2006, 105-109.

(56) References Cited

OTHER PUBLICATIONS

Li, et al. "Design, simulation and optimization of a miniaturized device for size-fractioned DNA extraction." Electrophoresis, 2007, 28(24):4661-4667.
Li, et al. "On-chip fraction collection for multiple selected ssDNA fragments using isolated extraction channels." Journal of Chromatography A, 2011, 1218(7): 997-1003.
Lin, et al. "Addressable Electric Fields for Size-Fractioned Sample Extraction in Microfluidic Devices." Anal. Chem., 2005, 77(14):4338-4347.
Lin, et al. "Selective extraction of size-fractioned DNA samples in microfabricated electrophoresis devices." Journal of Chromatography A, 2003, 1010(2):255-268.
Liu, et al. "DNA fragment analysis by an affordable multiple-channel capillary electrophoresis system." Electrophoresis, 2003, 24(1-2):93-95.
Liu, et al. "pK-Matched Running Buffers for Gel Electrophoresis." Analytical Biochemistry, 1999, 270(1):112-122.
Loutherback, et al. "Deterministic Microfluidic Ratchet." Physical Review Letters, Jan. 30, 2009, 102(4):045301-1-045301-4.
Loutherback, et al. "Deterministic separation of cancer cells from blood at 10 ml/min." AIP Advances, 2012, 2:042107-1-042107-7.
Loutherback, et al. "Improved performance of deterministic lateral displacement arrays with triangular posts." Microfluid Nanofluid, 2010, 9(6):1143-1149.
Lundqvist, et al. "Electrophoretic separation and confocal laser-induced fluorescence detection at ultralow concentrations in constricted fused-silica capillaries." Electrophoresis, 2003, 24(11):1737-1744.
Mali., et al. "RNA-Guided Human Genome Engineering via Cas9." Science, Feb. 15, 2013, 339(6121):823-826.
Margulies M., et al. "Genome Sequencing in Microfabricated High-density Picolitre Reactors." Nature, Sep. 15, 2005, 437(7057):376-380.
Marshall, et al. "Analytical Micro-preparative Electrophoresis: Quantitation of Phosphoglucose Isomerase Isoenzymes." Analytical Biochemistry, 1978, 91(1):283-292.
Maydan, et al. "Electrophoretic High Molecular Weight DNA Purification Enables Optical Mapping." Boreal Genomics, 2013, 1 page.
Meyer, et al. "Expanding Proteome Coverage with Orthogonal-specificity α-Lytic Proteases." Molecular & Cellular Proteomics, 2014, 13(3):823-835.
Minalla, et al. "Automated DNA fraction collection on glass microchips." Micro Total Analysis Systems, 2002, 2:946-948.
Morris, et al. "Fusion of a kinase gene, ALK, to a nucleolar protein gene, NPM, innon-Hodgkin's lymphoma." Science, 1994, 263(5151):1281-1284.
Morton, et al. "Crossing microfluidic streamlines to lyse, label and wash cells." Lab Chip, 2008, 8(9):1448-1453.
New England_Restriction_Buffer, NEBuffer Performance Chart with Restriction Enzymes. 2013 [online], [Retrieved on May 23, 2017]. Retrieved from the Internet: URL:https://www.neb.com/-/media/NebUs/Files/nebuffer-performance-chart-with-restrictionenzymes.pdf, 9 pages.
Nolin, et al. "Expansion of the Fragile X CGG Repeat in Females with Premutationor Intermediate Alleles." Am. J. Hum. Genet., 2003, 72(2):454-464.
Noolandi, et al. "Preparation, Manipulation, and Pulse Strategy for One-Dimensional Pulsed-Field Gel Electrophoresis (ODPFGE)." 1992, Chapter 7, 73-103 and Chapter 10, 135-143.
Olsen, et al. "Trypsin Cleaves Exclusively C-terminal to Arginine and Lysine Residues." Molecular & Cellular Proteomics, 2004, 3(6):608-614.
Olson, et al. "The Structure of Isometric Capsids of Bacteriophage T4." Virology, 2001, 279(2):385-391.
O'Sullivan T.F., et al. "Comparison of *Streptococcus thermophilus* Strains by Pulse Field Gel Electrophoresis of Genomic DNA." FEMS Microbiology Letters, Nov. 1998, 168(2):213-219.
Pamme, "Continuous flow separations in microfluidic devices." Lab Chip, 2007, 7(12):1644-1659.
Pelletier, et al. "Physical manipulation of the *Escherichia coli* chromosome reveals its soft nature." PNAS USA, Sep. 14, 2012, 109(40):E2649-E2656.
Persat, et al. "Purification of Nucleic Acids from Whole Blood Using Isotachophoresis." Anal. Chem., 2009, 81(22):9507-9511.
Peterson, et al. "Synthesis and oligomerization of N-Boc-N-(thymin-1-ylacetyl)ornithine." Bioorganic and Medical Chemistry Letters, 1996, 6(7):793-796.
Petty, et al. "Characterization of DNA size determination of small fragments by flow cytometry", Anal. Chem., 1995, 67:1755-1761.
Pluen, et al. "Diffusion of Macromolecules in Agarose Gels: Comparison of Linear and Globular Configurations." Biophysical Journal, Jul. 1999, 77(1): 542-552.
Rampino, et al. "Apparatus for Gel Electrophoresis with Continuous Monitoring of Individual DNA Molecules by Video Epifluorescence Microscopy." Analytical Biochemistry, 1991, 194(2):278-283.
Ren, et al. "A Simplified Method to Prepare PCR Template DNA for Screening of Transgenic and Knockout Mice." Comtemp Top Lab Anim. Sci., Mar. 2001, 40(2):27-30.
Riehn, et al. "Restriction mapping in nanofluidic devices." PNAS, Jul. 19, 2005, 102(29):10012-10016.
Ritti and Perbal, "Enzymes used in molecular biology: a useful guide." Journal of Cell Communication and Signaling, 2008, 2(1-2):25-45.
Robertson, et al. "Diffusion of isolated DNA molecules: Dependence on length and topology." PNAS, May 9, 2006, 103(19):7310-7314.
Rothberg, et al. "An integrated semiconductor device enabling non-optical genome sequencing," Nature, Jul. 21, 2011, 475(7356):348-52.
Scharenberg, et al. "Genome Engineering with TAL-Effector Nucleases and Alternative Modular Nuclease Technologies." Current Gene Therapy, 2013, 13(4):291-303.
Schoch, et al. "Rapid and selective extraction, isolation, preconcentration, and quantitation of small RNAs from cell lysate using on-chip isotachophoresis." Lab on a Chip, Apr. 28, 2009, 9:2145-2152.
Shalem, et al. "Genome-scale CRISPR-Cas9 Knockout Screening in Human Cells." Science, Jan. 3, 2014, 343(6166):84-87.
SIGMA_P8340, Protease Inhibitor Cocktail for use with mammalian cell and tissue extracts. Catalog No. P8340. Sigma-Aldrich. 2010 [online], [Retrieved on Mar. 20, 2017], Retrieved from the Internet: URL: https://www.sigmaaldrich.com/content/dam/sigmaaldrich/docs/Sigma/Datasheet/5/p8340dat.pdf, 1 page.
Singh-Gasson, et al. "Maskless fabrication of light-directed oligonucleotide microarrays using a digital micromirror array." Nature Biotechnology, 1999, 17(10):974-978.
Smith, et al. "A Physical Map of the *Escherichia coli* K12 Genome." Science, 1987, 236(4807):1448-1453.
Stoddard, "Homing Endonucleases: From Microbial Genetic Invaders to Reagents for Targeted DNA Modification." Structure, Jan. 12, 2011, 19(1):7-15.
Suh, et al. "Semi-automated quantification of C9orf72 expansion size reveals inverse correlation between hexanucleotide repeat number and disease duration in frontotemporal degeneration." Acta Neuropathol., Sep. 2015, 130(3):363-372.
Sun, et al. "Electrophoretic chip for high-fidelity fractionation of double-stranded DNA." Electrophoresis, 2007, 28(10):1572-1578.
Sutherland, et al. "Electronic Imaging System for Direct and Rapid Quantitation of Fluorescence from Electrophoretic Gels: Application to Ethidium Bromide-Stained DNA", Analytical Biochemistry, 1987, 163(2):446-457.
Tabak, et al. "A method for the recovery of DNA from agarose gels." Nucleic Acids Research, Jul. 1978, 5(7):2321-2332.
Tan, et al. "Gel Electrophoresis: DNA Science without the DNA!." Biochemistry and Molecular Biology Education, 2007, 35(5):342-349.
Tang, et al. "Compression and self-entanglement of single DNA molecules under uniform electric field." PNAS, Sep. 27, 2011, 108(39):16153-16158.
Tarn, et al. "On-chip processing of particles and cells via multilaminar flow streams." Anal. Bioanal. Chem., 2014, 406:139-161.

(56) References Cited

OTHER PUBLICATIONS

Tegenfeldt, et al. "The dynamics of genomic-length DNA molecules in 100-nm channels." PNAS, Jul. 27, 2004, 101(30):10979-10983.
Tomkinson, et al. "Location of the active site for enzyme-adenylate formation in DNA ligases." PNAS USA, Jan. 1991, 88(2):400-404.
Urnov, et al. "Genome editing with engineered zinc finger nucleases." Nature Reviews, Genetics, Sep. 2010, 11:636-646.
Volkmuth, et al. "DNA electrophoresis in microlithographic arrays." Nature, Aug. 13, 1992, 358(6387):600-602.
Wang, et al. "PacBio-LITS: a large-insert targeted sequencing method for characterization of human disease-associated chromosomal structural variations." BMC Genomics, 2015, 16(214):1-12.
Wang, et al. "A simple microfluidic system for efficient capillary electrophoretic separation and sensitive fluorimetric detection of DNA fragments using light-emitting diode and liquid-core waveguide techniques." Electrophoresis, 2005, 26(19):3602-3608.
Wang, et al. "IRDL Cloning: A One-Tube, Zero-Background, Easy-to-Use, Directional Cloning Method Improves Throughput in Recombinant DNA Preparation." PLoS One, Sep. 2014, 9(9):e107907:1-9.
Wang, et al. "Stretching DNA with optical tweezers." Biophysical Journal, Mar. 1997, 72(3):1335-1346.
Wang, et al. "Genetic screens in human cells using the CRISPR/Cas9 system." Science, Jan. 3, 2014, 343(6166):80-84 (12 pages total).
Wang, et al. "Study of Preparation and Restriction Endonuclease of B. cepacia HMW DNA", Biotechnology Bulletin, Dec. 31, 2009, Issue 3, 137-142 (with English Abstract).
Wilson, et al. "Engineered DNA ligases with improved activities in vitro." Protein Engineering, Design & Selection, 2013, 26(7):471-478.
Worcel, et al. "On the Structure of the Folded Chromosome of Escherichia coli." J. Mol. Biol., 1972, 71(2):127-147.
Xiao, et al. "CE with LED-based detection: An update." Electrophoresis, Aug. 24, 2008, 30(1):189-202.
Zakharov, et al. "Recovery of SDS-protein and DNA using commercial automated gel electrophoresis apparatus", Applied and Theoretical Electrophoresis, 1995, 5(1):25-29.
Zalewski, et al. "Electrokinetic sorting and collection of fractions for preparative capillary electrophoresis on a chip", Lab on a Chip, 2008, 8(5):801-809.
Zaret, et al. "Micrococcal Nuclease Analysis of Chromatin Structure." Curr. Protoc. Mol. Biol., 2005, 21.1.1 (Supplement 69):1-17.
Zetsche, et al. "Cpf1 is a single RNA-guided endonuclease of a class 2 CRISPR-Cas system," Cell, Oct. 22, 2015, 163(3):759-771.
Zhang, et al., "Isolation of the HMW-DNA from Crofton Weed (Ageratina adenophora)", Acta Bot. Boreal. -Occident. Sin., Dec. 31, 2011, 31(12):2551-2557 (with English Abstract).
Zimmerman and Minton, "Macromolecular Crowding: Biochemical, Biophysical, and Physiological Consequences." Annu. Rev. Biophys. Biomol. Struct., 1993, 22(1):27-65.
Anders et al.. "In vitro enzymology of Cas9. Methods Enzymol." 2014; 546:1-20. doi: 10.1016/B978-0-12-801185-0.00001-5.
Archer, CT. et al., "The genome sequence of E. coli W (ATCC 9637): comparative genome analysis and an improved genome-scale reconstruction of E. coli," BMC Genomics, Jan. 6, 2011, 12(9), 20 pages.
Bjerrum et al., "Buffer systems and transfer parameters for semi dry electroblotting with a horizontal apparatus", Analytical electrophoresis, 1986: pp. 315-327.
Boles, TC et al., "Structure of plectonemically supercoiled DNA", J. Mol. Biol., Jun. 20, 1990, 213(4): 931-51.
Cai, W. et al., "High-resolution restriction maps of bacterial artificial chromosomes constructed by optical mapping", Proc Natl Acad Sci USA, Mar. 31, 1998, 95(7): 3390-5.
Cametti et al. "The fluorous effect in biomolecular applications" Chem Soc Rev. Jan. 7, 2012;41(1): 31-42. doi: 10.1039/c1cs15084g. Epub Jun. 2, 20110.
Chen, Z et al. "Ultra-low input single tube linked-read library method enables short-read NGS systems to generate highly accurate and economical long-range sequencing information for de novo genome assembly and haplotype phasing," bioRxiv, 2019, 853947, doi: https://doi.org/10.1101/852947, 19 pages.
Chu et al. "Second-generation tags for fluorous chemistry exemplified with a new Fluorous Mitsunobu reagent" Org Lett. Jun. 1, 20089;10(12):2453-6. doi: 10.1021/01800750q. Epub May 1, 20087.
Collins et al.An exhaustive DNA micro-satellite map of the human genome using high performance computing. Genomics. Jul. 2003;82(1): 10-9. doi: 10.1016/s0888-7543(03)00076-4.
Cornaggia et al. "Tagging molecules with linear polymers: Biocatalytic transformation of substrates anchored on soluble macromolecules". Comb Chem High Throughput Screen. Jan. 2010;13(1): 45-53. doi: 10.2174/138620710790218177.
Deangelis, Mm et al., "Solid-phase reversible immobilization for the isolation of PCR products", Nucleic Acids Res., Nov. 25, 1995, 23(22): 4742-3.
Demidov et al.. "Duplex DNA capture" Curr Issues Mol Biol. Jan. 2000; 2(1):31-5.
Ellegren et al. "Microsatellites: simple sequences with complex evolution" Nat Rev Genet. Jun. 2004; 5(6): 435-45. doi: 10.1038/nrg1348.
Francia, MV et al., "A classification scheme for mobilization regions of bacterial plasmids", FEMS Microbiol. Rev., Feb. 2004, 28(1): 79-100.
Fregel, R et al., "Improved ethanol precipitation of DNA", Electrophoresis, 2010, 31: 1350-1352.
Gross-Bellard et al. "Isolation of high-molecular-weight DNA from mammalian cells" Eur J Biochem. Jul. 2, 1973; 36(1): 32-8. doi: 10.1111/j.1432-1033.1973.tb02881.x.
International Preliminary Report on Patentability for International Application No. PCT/US2021/028922 dated Nov. 3, 2022, 9 pages.
International Search Report and Written Opinion issued in PCT/US2021/028922, dated Aug. 6, 2021, 12 pages.
Kuhn et al. "Hybridization of DNA and PNA molecular beacons to single-stranded and double-stranded DNA targets" J Am Chem Soc. Feb. 1, 20023;124(6): 1097-103. doi: 10.1021/ja0041324.
Mikheikin, A. et al. "DNA nanomapping using CRISPR-Cas9 as a programmable nanoparticle", Nat. Commun., Nov. 21, 2017, 8(1): 1665.
Møller, H.D. et al. "Circular DNA elements of chromosomal origin are common in healthy human somatic tissue", Nature Communications, 2018, 9(1069): 1-12.
Panza et al. "Fluorinated NAD as an affinity surfactant" Chem Commun (Camb). May 7, 2002; (9): 928-9. doi: 10.1039/b201729f. PMID: 12123052.
Pilla, G et al., "Going around in circle: virulence plasmids in enteric pathogens", Nat Rev. Microbiol., Aug. 2018, 16(8): 484-495.
Rozwandowicz, M et al., "Plasmids carrying antimicrobial resistance genes in Enterobacteriaceae", J. Antimicrob Chemother., May 2018, 73(5): 1121-1137.
Shepard et al. "Magnetic bead capture of cDNAs from double-stranded plasmid cDNA libraries" Nucleic Acids Res. Aug. 1, 1997; 25(15): 3183-5. doi: 10.1093/nar/25.15.3183.
Sherratt D.J. "Bacterial plasmids", Cell, Nov. 1974, 3(3): 189-95.
Spietelun et al. "Green aspects, developments and perspectives of liquid phase microextraction techniques." Talanta. Feb. 2014; 119:34-45. doi: 10.1016/j.talanta.2013.10.050. Epub Oct. 2, 20139.
Studer et al."Fluorous synthesis: a fluorous-phase strategy for improving separation efficiency in organic synthesis" Science. Feb. 7, 1997; 275(5301): 823-6.
Towbin et al. "Immunoblotting and dot immunobinding—current status and outlook" J Immunol Methods. Sep. 4, 1984; 72(2): 313-40.
Towbin, H. et al., "Electrophoretic transfer of proteins from polyacrylamide gels to nitrocellulose sheets: procedure and some applications," Proc. Nat. Acad. Sci. USA, 76(9):4350-4354 (1979).
Veltri, KL et al., "Distinct genomic copy No. in mitochondria of different mammalian organs", J. Cell Physiol., Apr. 1990, 143(1): 160-4.
Verhaak, RGW et al., "Extrachromosomal oncogene amplification in tumor pathogenesis and evolution," Nat Rev. Cancer, 2019, 19(5): 283-288.

(56) References Cited

OTHER PUBLICATIONS

Wetmur, JG "Dna probes: applications of the principles of nucleic acid hybridization" Crit Rev Biochem Mol Biol. 1991; 26(3-4): 227-59. doi: 10.3109/10409239109114069.

Wu, S. et al., "Circular ecDNA promotes accessible chromatin and high oncogene expression", Nature, Nov. 2019, 575(7784): 699-703.

Zhang, W. Fluorous tagging strategy for solution-phase synthesis of small molecules, peptides and oligosaccharides. Curr Opin Drug Discov Devel. Nov. 2004; 7(6): 784-97.

* cited by examiner

In this drawing, ">" symbolizes a simple sequence repeat unit (for instance, $G_4C_2$ in the ALS gene, C9orf72). In C9orf72, the threshold for the number of $G_4C_2$ repeats associated with disease phenotype is estimated to be somewhere between 30 and 70, although many affected individuals can have repeat expansions as large as 10's of kilobases (many thousands of repeat units).

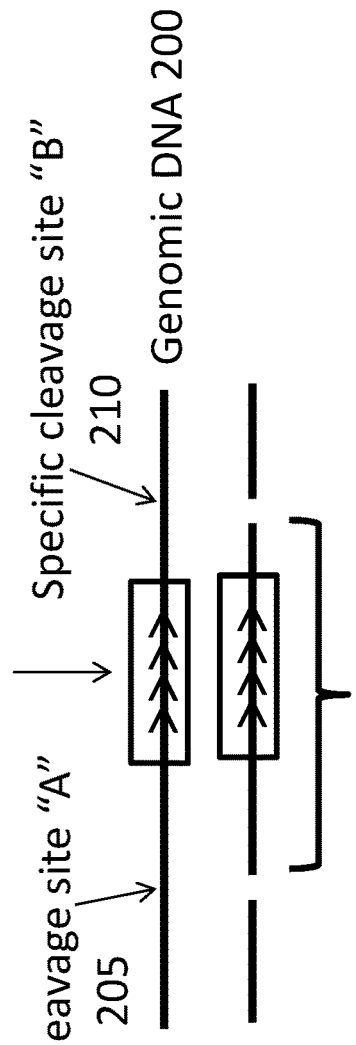
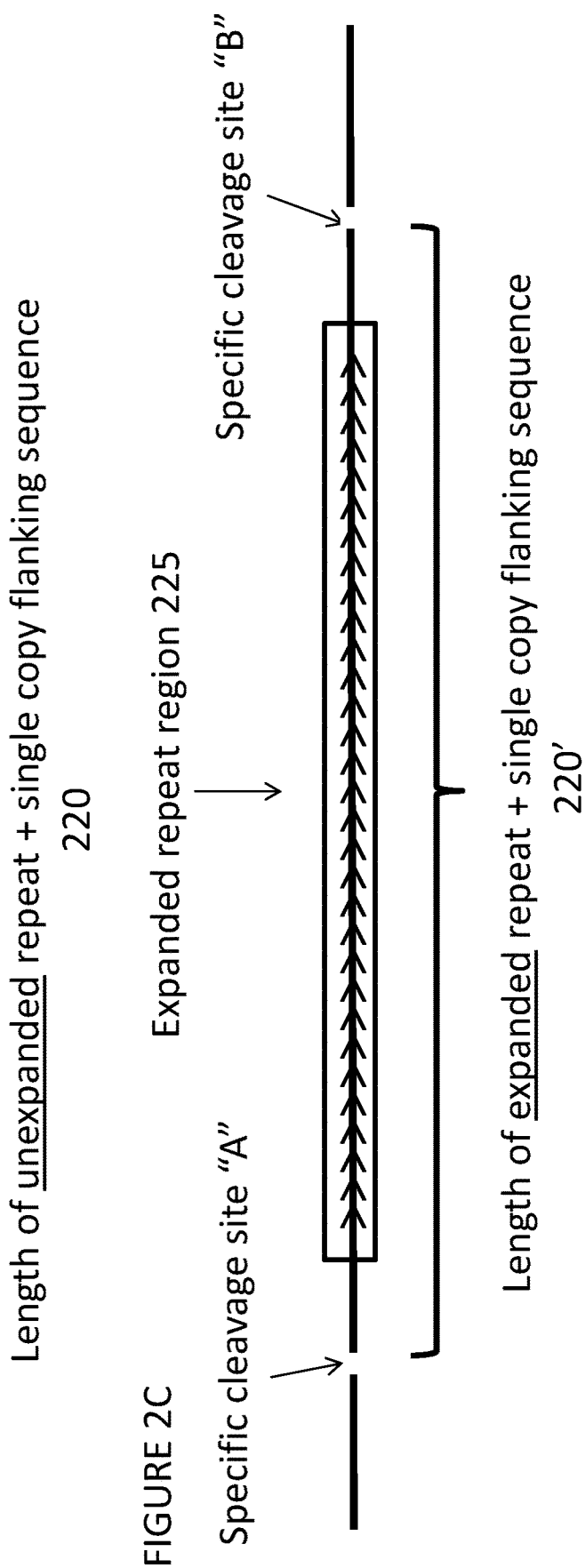
FIGURE 2A
FIGURE 2B
FIGURE 2C

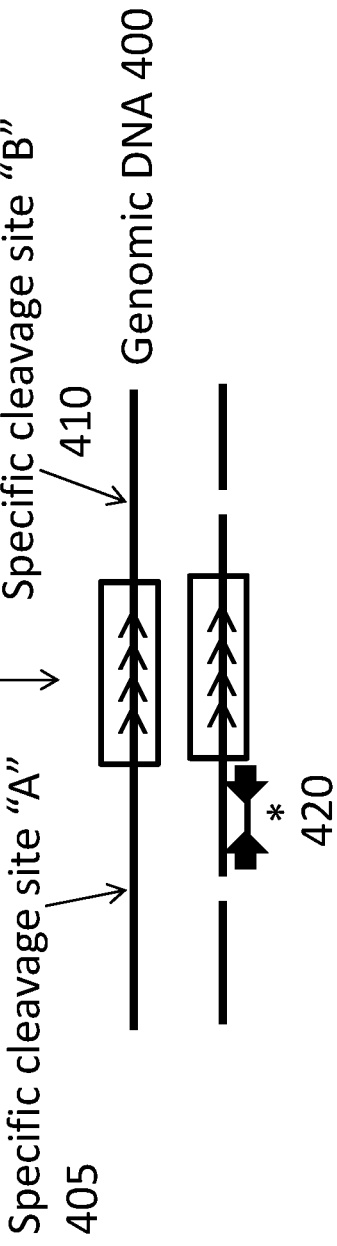
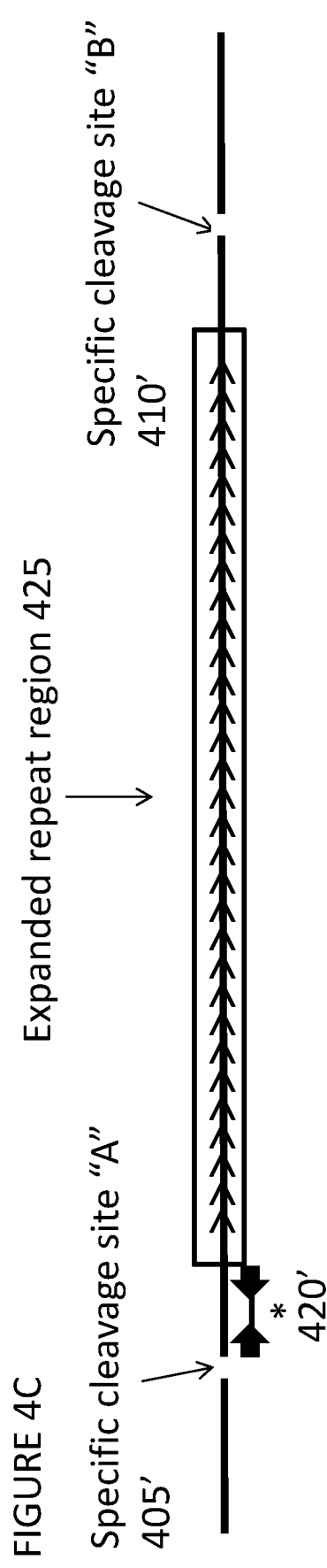
FIGURE 4A
FIGURE 4B
FIGURE 4C

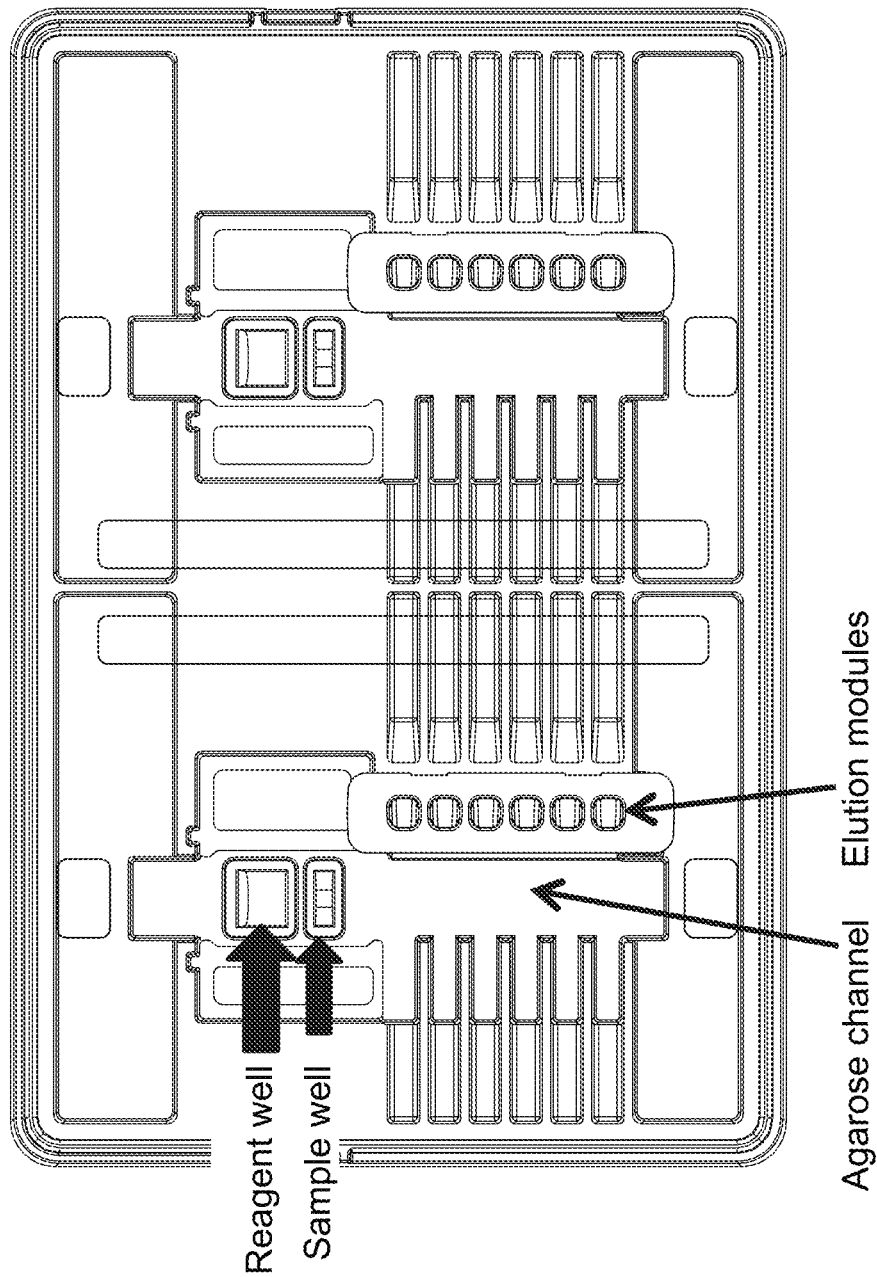
FIGURE 6  SageHLS Cassette (based on ELF), allows integration of DNA extraction and cleavage steps. 2 samples per cassette. 6 elution modules (size fractions) per lane. Size-separation straight down, electroelution of product rightward (in view shown). Cassette has standard SBS multwell plate footprint.

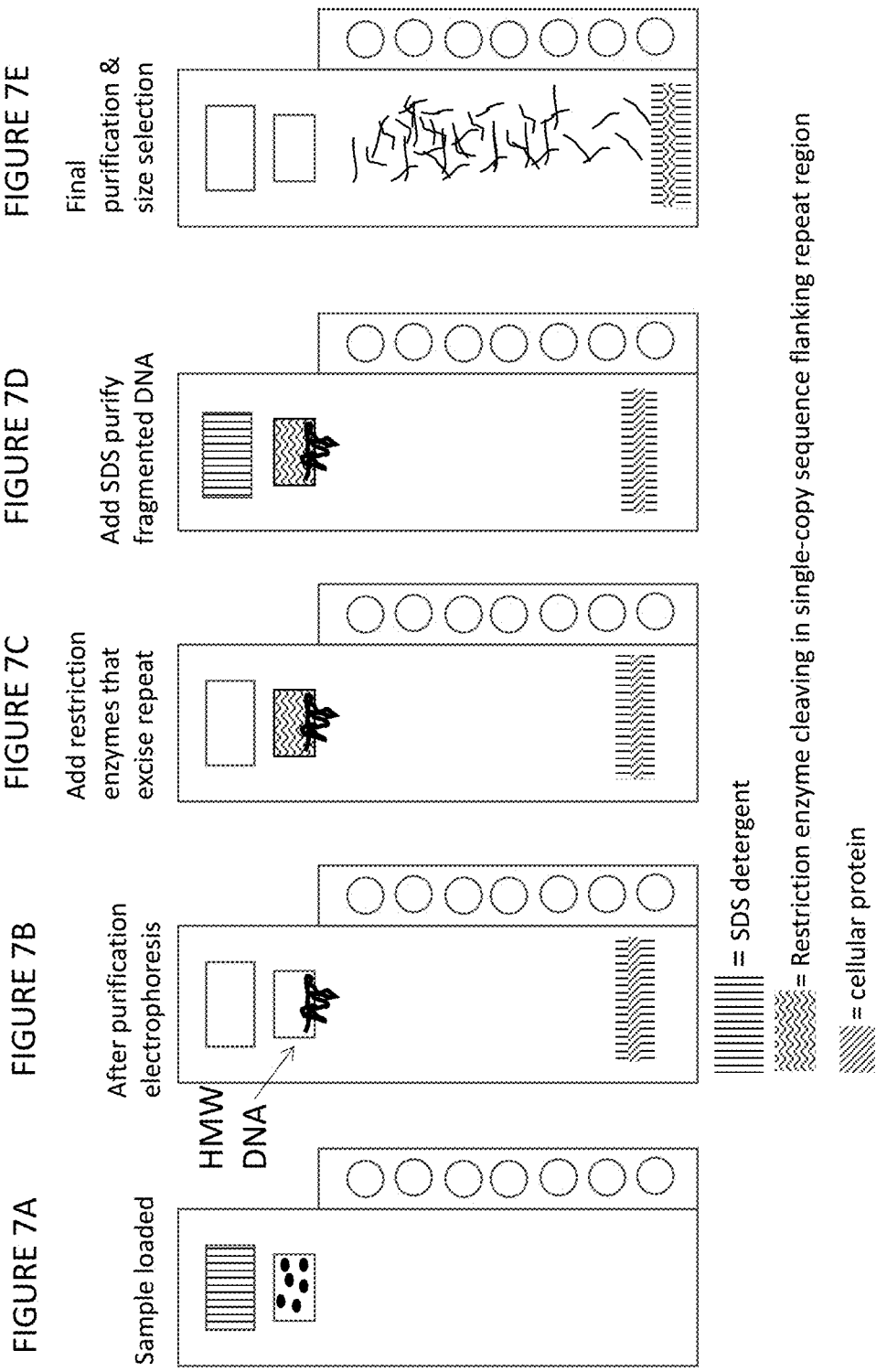

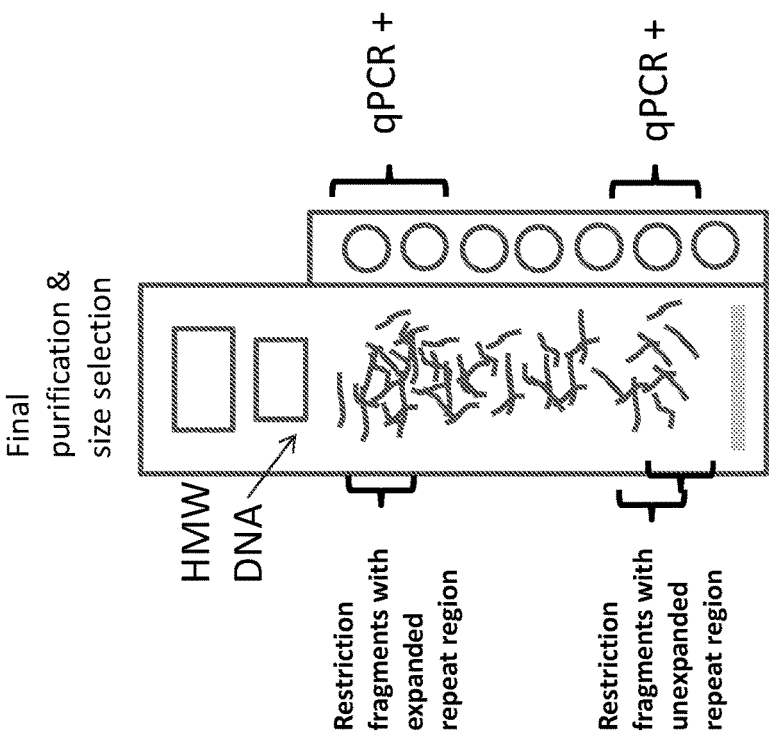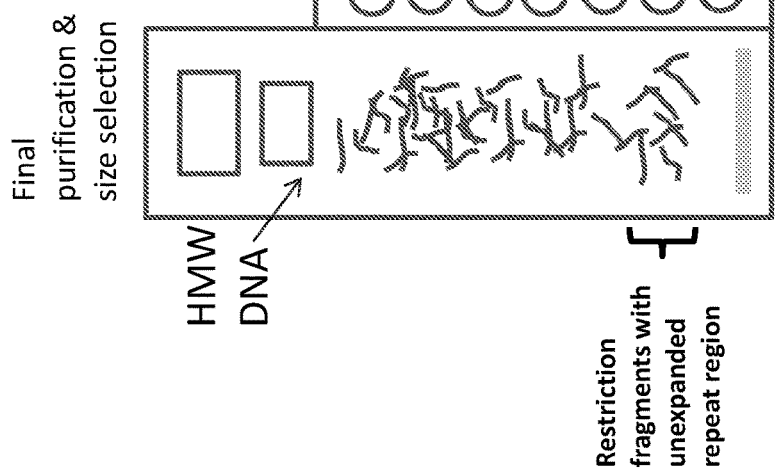

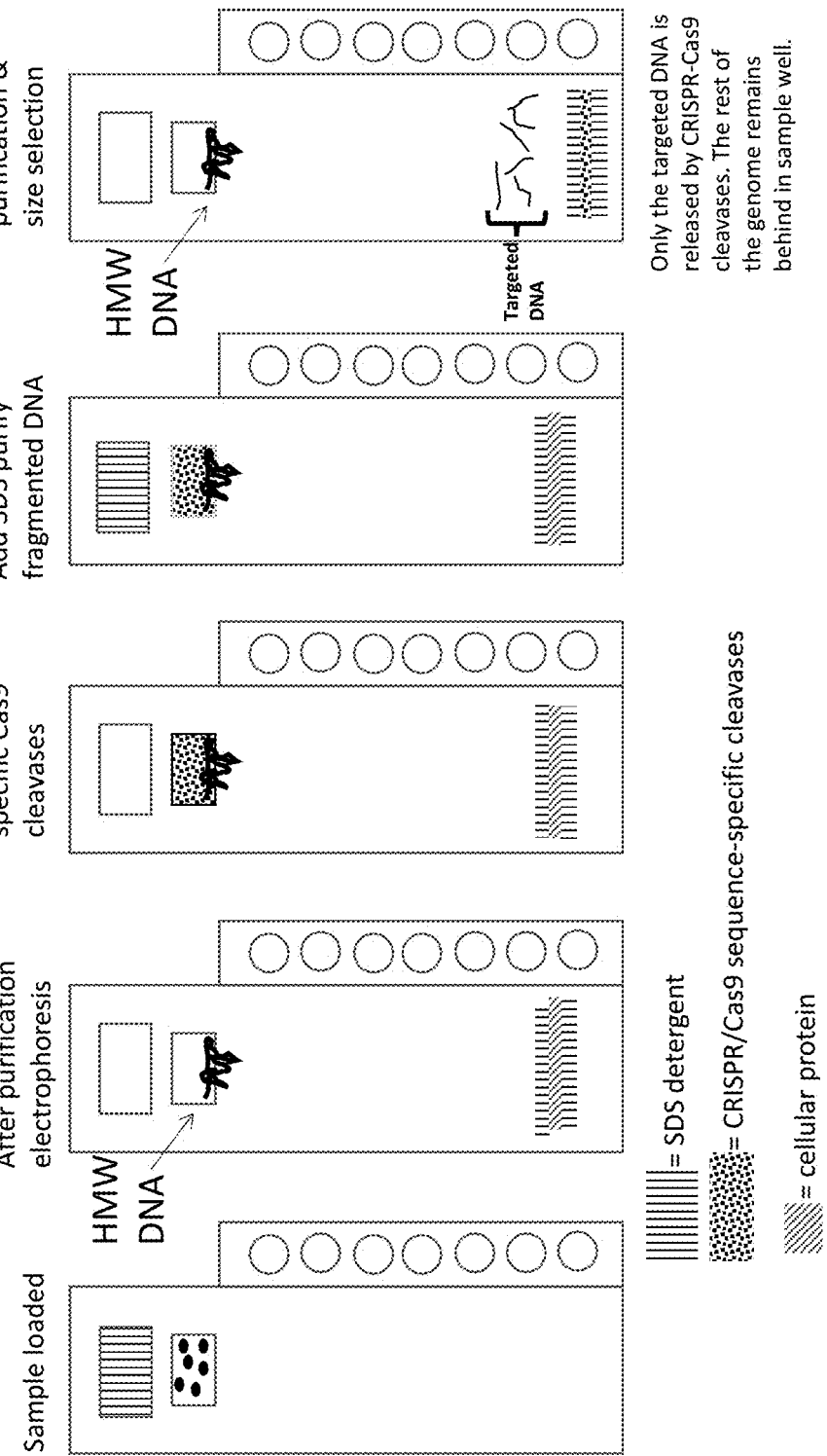

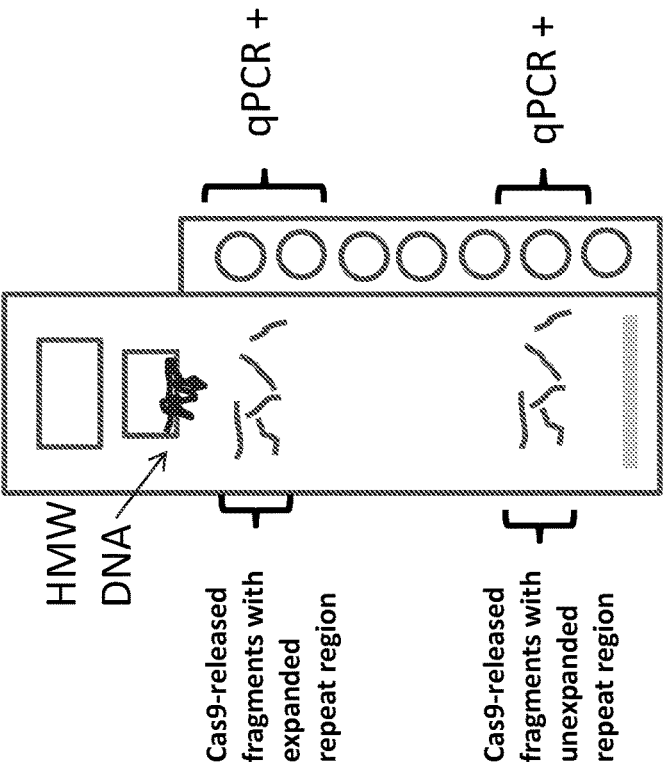
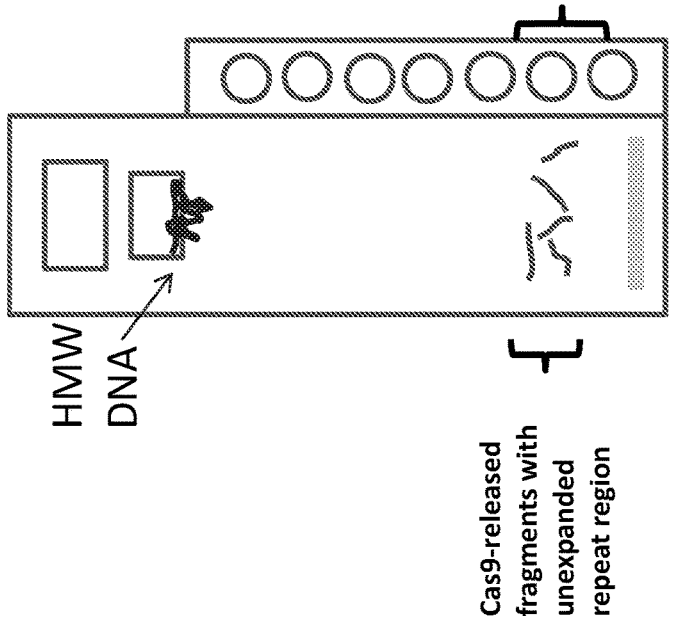

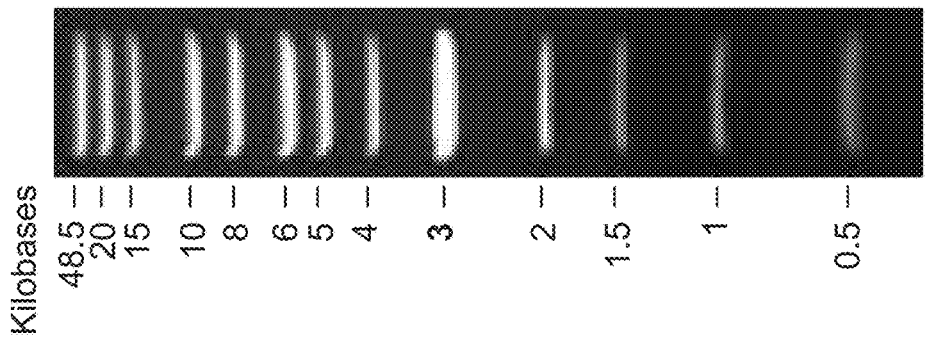
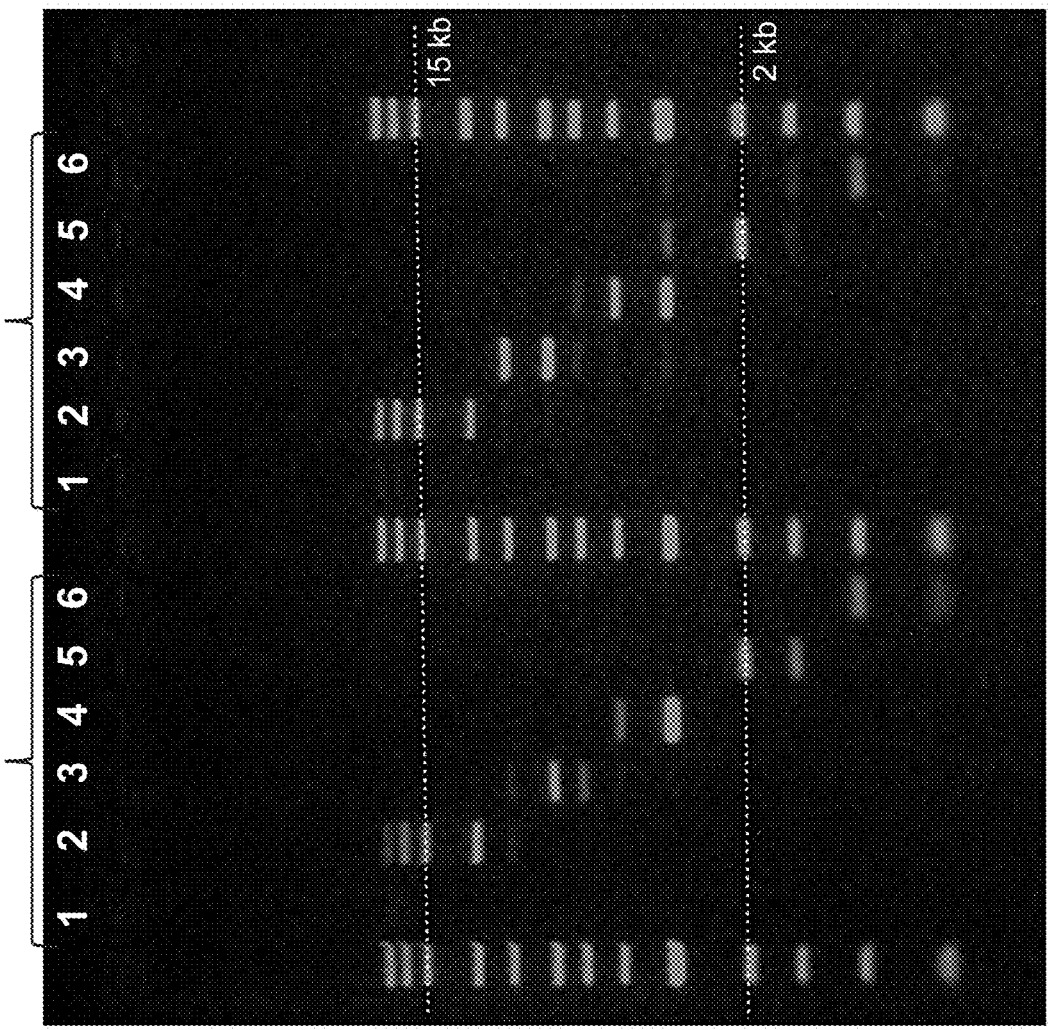

Targeted BRCA1 200kb fragment was found in fraction 3.
Total yield was about 1.5e06 copies (~200pg of 200kb frag).

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: BRCA1gR67 crRNA

<400> SEQUENCE: 1

```
gcttattaca ttctcggcca                                               20

<210> SEQ ID NO 2
<211> LENGTH: 20
<212> TYPE: DNA
<213> ORGANISM: Artificial Sequence
<220> FEATURE:
<223> OTHER INFORMATION: BRCA1gR68 crRNA

<400> SEQUENCE: 2
cttattacat tctcggccat                                               20

<210> SEQ ID NO 3
<211> LENGTH: 20
<212> TYPE: DNA
<213> ORGANISM: Artificial Sequence
<220> FEATURE:
<223> OTHER INFORMATION: BRCA1gR69 crRNA

<400> SEQUENCE: 3
attacattct cggccatggg                                               20

<210> SEQ ID NO 4
<211> LENGTH: 20
<212> TYPE: DNA
<213> ORGANISM: Artificial Sequence
<220> FEATURE:
<223> OTHER INFORMATION: BRCA1gLL1 crRNA

<400> SEQUENCE: 4
cctctgggag ccacaggcca                                               20

<210> SEQ ID NO 5
<211> LENGTH: 20
<212> TYPE: DNA
<213> ORGANISM: Artificial Sequence
<220> FEATURE:
<223> OTHER INFORMATION: BRCA1gLL3 crRNA

<400> SEQUENCE: 5
gccatgacaa caacccagac                                               20
```

SYSTEMS AND METHODS FOR DETECTION OF GENETIC STRUCTURAL VARIATION USING INTEGRATED ELECTROPHORETIC DNA PURIFICATION

CROSS-REFERENCE TO RELATED APPLICATIONS

This application is a National Stage Entry and is entitled to and hereby claims priority under 35 U.S.C. §§ 365 and 371 to corresponding PCT Application No. PCT/US2018/026603, filed Apr. 6, 2018 entitled "Systems and Methods for Detection of Genetic Structural Variation Using Integrated Electrophoretic DNA Purification", and also claims priority to and benefit of U.S. Provisional Patent Application No. 62/483,261, filed Apr. 7, 2017, and entitled "Systems and Methods for Detection of Genetic Structural Variation Using Integrated Electrophoretic DNA Purification." The present application incorporates herein by reference each disclosure of the above-referenced applications in its entirety.

INCORPORATION BY REFERENCE OF SEQUENCE LISTING

The contents of the file named "SAGS-015_N01US_SeqListing_ST25.txt", which was created on Jan. 6, 2022, and is 1.34 KB in size are hereby incorporated by reference in their entirety.

BACKGROUND

Many inherited genetic diseases are caused by length expansions of chromosomal regions containing simple DNA sequence repeats. For instance, the mental retardation syndrome, fragile X, is caused by and expansion of a $(CGG)_n$ sequence near the 5' end of the gene FMR1 from <50 CGG copies in most unaffected individuals to more than 200 copies in most affected individuals (Nolin et al., 2003). Similarly, in the most commonly mutated gene associated with ALS, C9orf72, expansion of a $(G_4C_2)_n$ repeat in the first intron from <8 repeats to ≥300 repeats, is associated with the disease state (Suh, et al., 2015). At least twenty-two inherited neurological diseases are caused by such repeat expansion mutations (La Spada and Taylor, 2010).

Detection and analysis of such repeat expansion mutations can be complicated by several factors. First, PCR amplification of regions containing simple sequence repeat 2-10 bp in length is error-prone, usually producing a family of amplicon products that differs in the number of repeat units. Many repeat expansions are also extremely GC-rich, which makes development of PCR assays even more difficult. With careful optimization for specific genome loci, these problems can be minimized so that useful diagnostic assays can be obtained, but such optimization of assays is laborious and time-consuming, and the conditions for one repeat expansion type are frequently not transferable to other assays.

Another difficulty with PCR assays is that some repeat expansions can be >20 kb in size (Nolin et al., 2003), beyond the typical size range of PCR assays which generally found to be somewhere between 5-10 kb. This means that alleles with very large expansions might go undetected in PCR assays.

To avoid these complications, Southern blot analyses are still used in many cases, particularly where repeat expansions can be many kb in size. However, routine use of Southern blots is extremely laborious and time consuming, and time to result can be two-to-four days, including blot analysis time.

SUMMARY OF SOME OF THE EMBODIMENTS

Various apparatuses, systems, and methods are described herein. In some embodiments, an electrophoresis cassette may be provided. The electrophoresis cassette may comprise at least one sample well, at least one gel column that contains a separation gel, and a plurality of elution modules arranged next to the at least one gel column. A sample may be provided in the electrophoresis cassette. High-molecular weight (HMW) DNA may be isolated from the same, and single-copy DNA sequences may be cleaved on both sides of a repeat region of the DNA, thereby producing a cleaved sample. The cleaved sample may be fractionated using gel electrophoresis, and DNA fractions may be isolated from consecutive sections of the separation gel. The DNA fractions may be subjected to PCR assays to detect single-copy sequences within the DNA fraction, said single-copy sequence containing repeat expansion sequences, and the subjected DNA fractions may be electroeluted into the plurality of elution modules. The size of DNA fractions having the repeat expansion sequences may be determined. It may be determined whether the size of the DNA fractions with the repeat expansion sequences is above a normal repeat size range.

The cleaving may be performed by restriction enzymes, and these enzymes may be configured not to cut within a repeat-containing fragment of DNA. Alternatively and/or additionally, the cleaving may be performed with customizable RNA or DNA directed cleavases, which may comprise Cas9, Cpf1, and NgAgo.

In some embodiments, liquid electrophoresis buffer may be provided in the plurality of elution modules of the electrophoresis cassette, such that the DNA fractions subjected to PCR assays are electroeluted into the plurality of elution modules are disposed in the electrophoresis buffer. The electrophoresis buffer with the DNA fractions may be added to a PCR reaction, and this may be assayed for single-copy sequence targets within the repeat expansion sequences.

Changing the conditions of electrophoresis, such as gel concentration, voltage, voltage waveform, buffer composition, and run time, may change the mobility of the DNA fractions. The conditions may be changed to slow DNA fragments over a predetermined length from electrophoresing far into the at least one gel column.

BRIEF DESCRIPTION OF THE FIGURES

FIGS. 2A-2B show length of an unexpanded repeat and single copy flanking sequence, according to some embodiments.

FIG. 2C shows length of an expanded repeat and single copy flanking sequence, according to some embodiments.

FIGS. 4A-4C show the location of a single copy qPCR detection amplicon, according to some embodiments.

FIG. 6 shows an exemplary SageHLS cassette, according to some embodiments.

FIGS. 7A-10B show exemplary workflows, according to various embodiments.

FIGS. 11A-11B shows electrophoresis conditions on the SageHLS cassette, according to some embodiments.

DETAILED DESCRIPTION OF SOME OF THE EMBODIMENTS

A procedure is disclosed herein for characterizing repeat expansion mutations that combines the broad size flexibility Southern blotting assays with detection by PCR. For many assay applications, the workflow can be completed in less than one day.

Figure 1A:
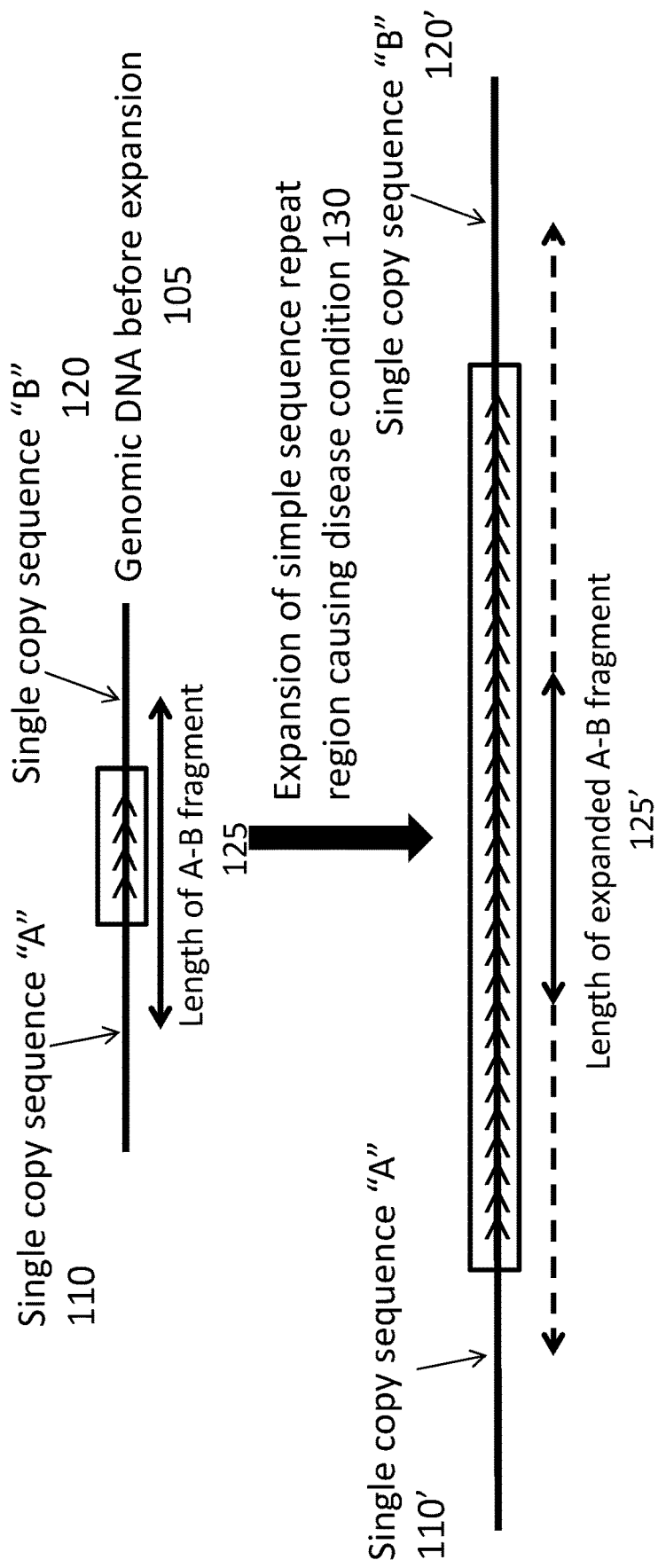
FIG. 1A shows expansion of a sequence repeat region, according to some embodiments.

FIG. 1A shows genomic DNA before expansion 105, which has a single copy sequence A 110, a chromosomal region containing simple sequence repeat 115, and single copy sequence B 120. The genomic DNA before expansion 105 has length 125. When the chromosomal region containing simple sequence repeat 115 is expanded, a disease condition may result 130. The expanded simple sequence repeat region 130 is surrounded by single copy sequence A 110' on one side and single copy sequence B 120' on the other. The length of the expanded A-B fragment 125' is longer than the length of A-B fragment 125.

As shown in the drawing, '>' symbolizes a simple sequence repeat unit. For example, this may be $G_4C_2$ in the ALS gene, C$_9$orf72. In C$_9$orf72, the threshold for the number of $G_4C_2$ repeats associated with disease phenotype is estimated to be somewhere between 30 and 70, although many affected individuals can have repeat expansions as large as tens of kilobases (many thousands of repeat units).

Figure 1B:
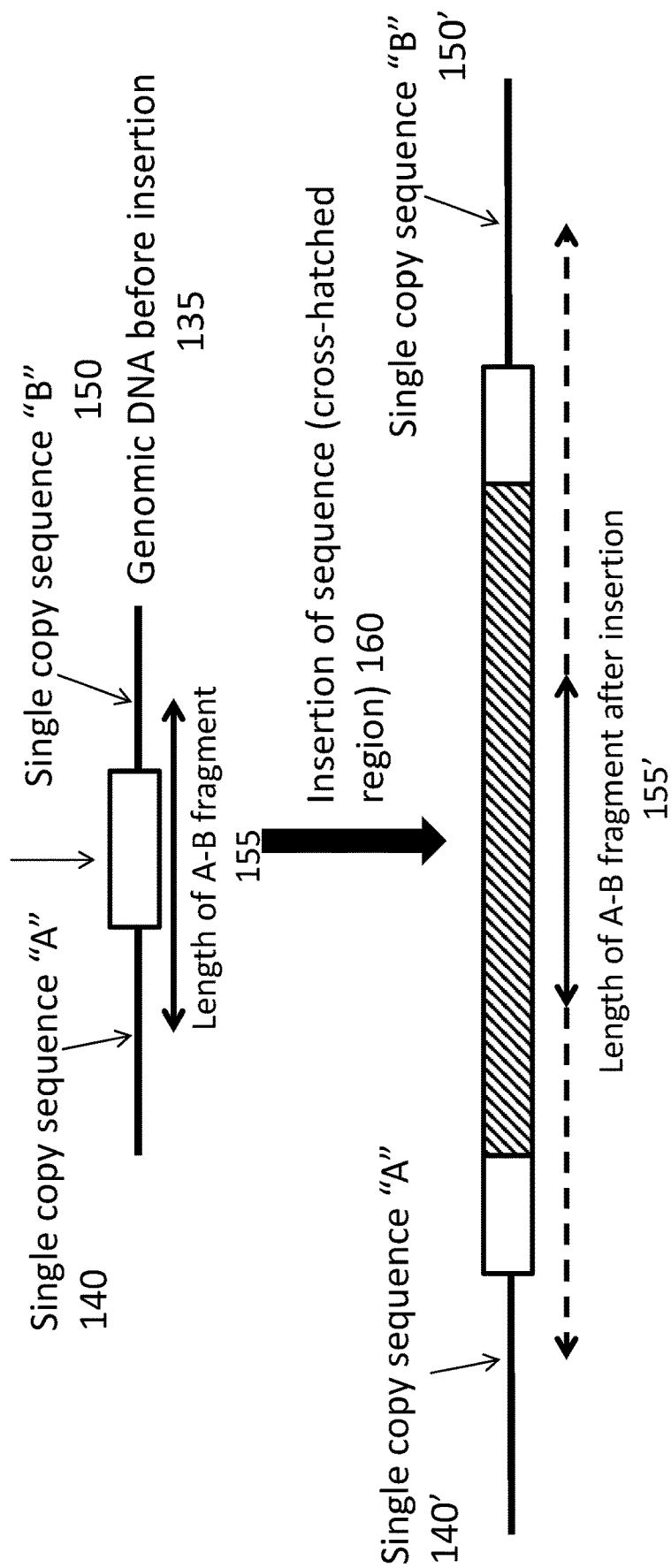
FIG. 1B shows insertion of a sequence, according to some embodiments.

FIG. 1B shows insertion of a sequence according to some embodiments. Here, the genomic DNA before insertion 135 has single copy sequence A 140, a chromosomal target site for insertion event 145, and single copy sequence B 150. The A-B fragment has length 155. A sequence is then inserted at the target site 160. After insertion, single copy sequence A 140' is on one side of the inserted sequence 160, and single copy sequence B 150' is on the other side. The resulting length of the A-B fragment 155' after insertion is longer than then length of A-B fragment 155.

Figure 1C:
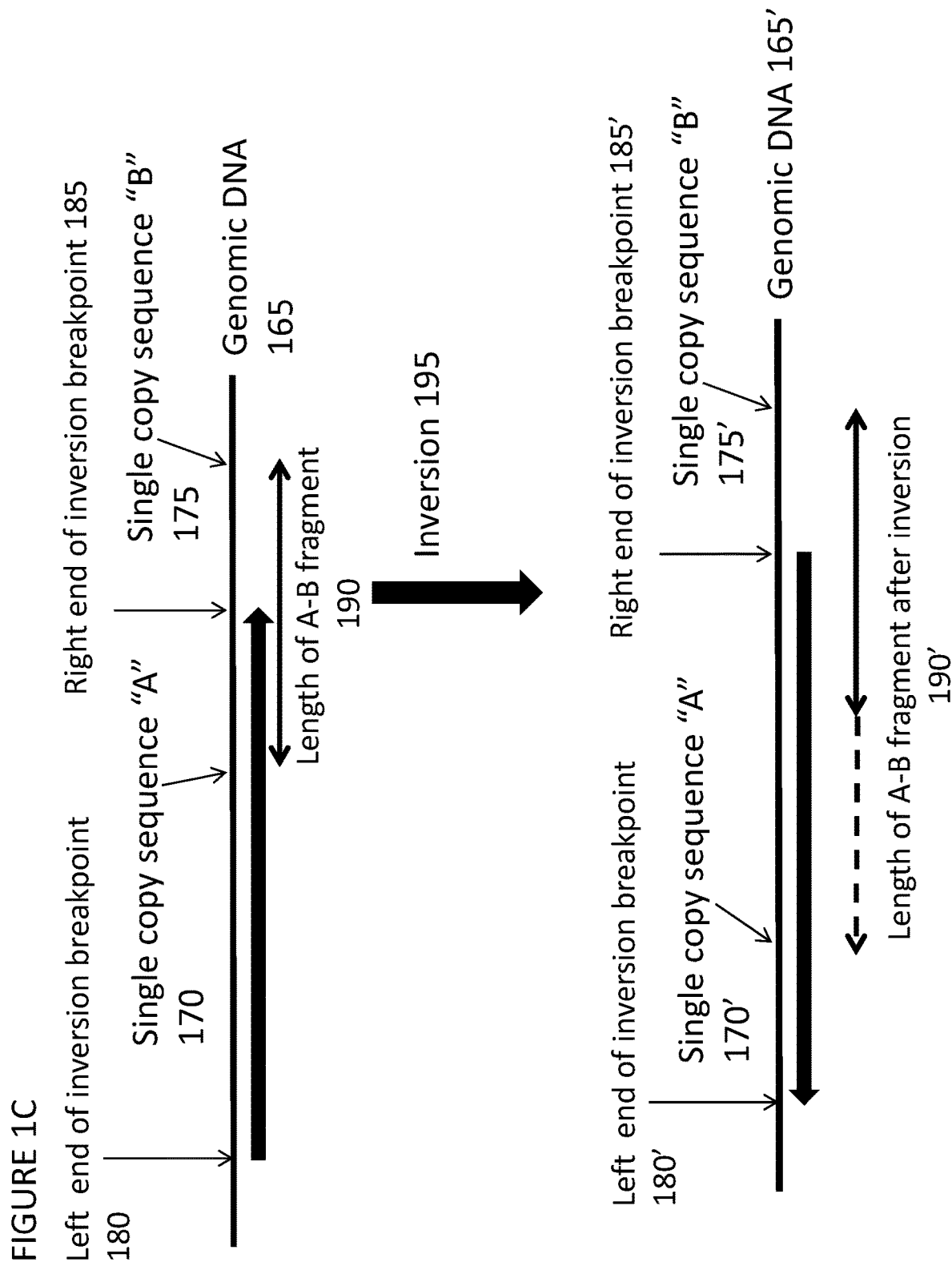
FIG. 1C shows inversion of a sequence, according to some embodiments.

FIG. 1C shows inversion of a sequence according to some embodiments. As shown, genomic DNA 165 has single copy sequence A 170 and single copy sequence B 175. Single copy sequence A 170 may be configured between a left end of an inversion breakpoint 180 and a right end of the inversion breakpoint 185. Single copy sequence B 175 may be configured outside of the inversion breakpoints 180, 185. The A-B fragment may have a length 190. A section between the left end of inversion breakpoint 180 and right end of inversion breakpoint 185 may be inverted 195. The resulting genomic DNA 165' may have single copy sequence A 170' and single copy sequence B 175' configured such that the length of the A-B fragment after inversion 190' is different from the length of A-B fragment 190. In some embodiments, such as the one shown in FIG. 1C, the length of the A-B fragment after inversion 190' may be longer than the length of the A-B fragment before inversion 190. In some embodiments, the length of the A-B fragment after inversion 190' may be shorter than the length of the A-B fragment before inversion 190.

FIG. 2A shows genomic DNA 200 having specific cleavage site A 205 and specific cleavage site B 210 before cleavage. A chromosomal region containing a repeat 215 is configured between cleavage site A 205 and cleavage site B 210. The length of the unexpanded repeat and single copy flanking sequence is shown 220. In FIG. 2B, the genomic DNA 200 has been cleaved at cleavage site A 205 and cleavage site B 210 such that the cleaved section has length 220. FIG. 2C shows the specific cleavage site A 205' and specific cleavage site B 210' with the expanded repeat region 225. The expanded repeat and single copy flanking sequence has length 220'.

Figure 3:
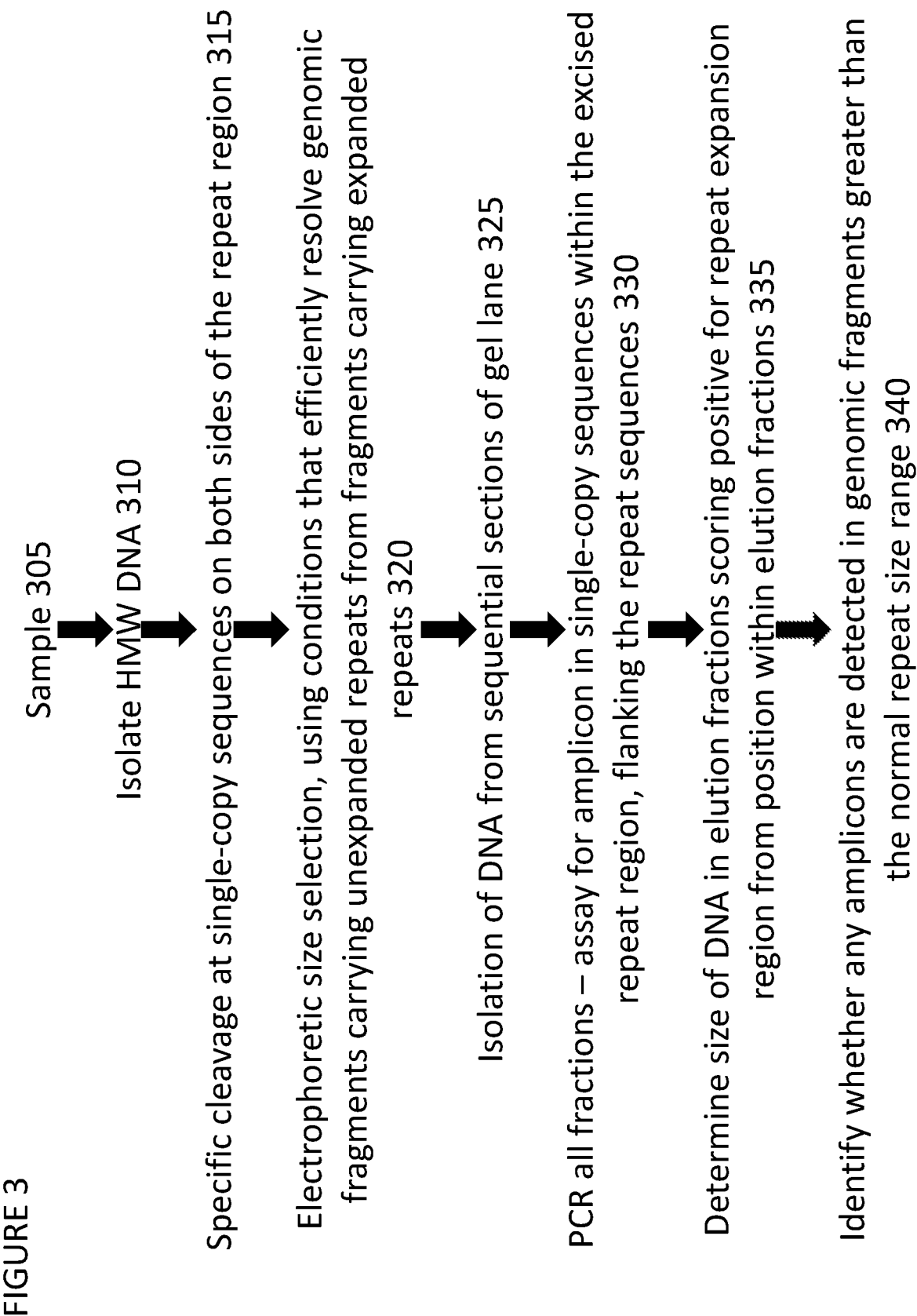
FIG. 3 shows an exemplary flow diagram, according to some embodiments.

An exemplary embodiment is shown in FIG. 3. A sample may be provided 305 and HMW DNA may be isolated from the sample 310. Specific cleavage may be performed at single-copy sequences on both sides of the repeat regions of the HMW DNA 315. The cleaved sample may be fractionated. In some embodiments, the cleaved sample is fractionated using gel electrophoresis. Electrophoretic size selection may be performed using conditions that efficiently resolve genomic fragments that carry unexpanded repeats from fragments that carry the expanded repeats 320. DNA may be isolated from sequential/consecutive sections of the separation gel and/or gel lane 325. DNA fractions may be subjected to PCR 330. The PCR may be assays for amplicon in single-copy sequences within the excised repeat region, flanking the repeat sequences. The size of DNA in elution fractions scoring positive for repeat expansion regions from position within elution fractions may be determined 335, and it may be determined whether any amplicons are detected in genomic fragments greater than the normal repeat size range 340.

In some embodiments, the basis of the assay is to measure the length of a DNA fragment that is produced by cleaving at unique single-copy DNA sequences on both sides of the repeat expansion region (FIG. 1A, FIGS. 2A-B). Fragments derived from unexpanded repeats will be smaller than fragments derived from expanded repeats. The cleaved sample is size fractionated by gel electrophoresis, and DNA is isolated from consecutive sections of the separation gel, including all gel regions occupied by the sample DNA. The purified DNA fractions are subjected to PCR assays that are designed to detect single-copy sequences within specifically released fragment that contains the repeat expansion sequences (FIGS. 4A-4C).

As shown in FIG. 4A, genomic DNA 400 is shown with specific cleavage site A 405 and specific cleavage site B 410. A chromosomal region containing repeat 140 is configured between specific cleavage site A 405 and specific cleavage site B 410. FIG. 4B shows cleavage at specific cleavage site A 405 and specific cleavage site B 410. Between specific cleavage site A 405 and the chromosomal region containing repeat 415 is a location of single copy qPCR detection amplicon 420. FIG. 4C shows the expanded repeat region 425 between specific cleavage site A 405' and specific cleavage site B 410'. The location of single copy qPCR detection amplicon 420' is shown.

The cleavages discussed throughout the disclosure (including in flanking single-copy sequence (FIGS. 2A-2C)) can be achieved by restriction enzymes, provided that they do not cut elsewhere within the repeat-containing fragment.

These cleavages can also be accomplished with customizable RNA or DNA directed cleavases such as Cas9, Cpf1, or NgAgo.

Figure 5A:
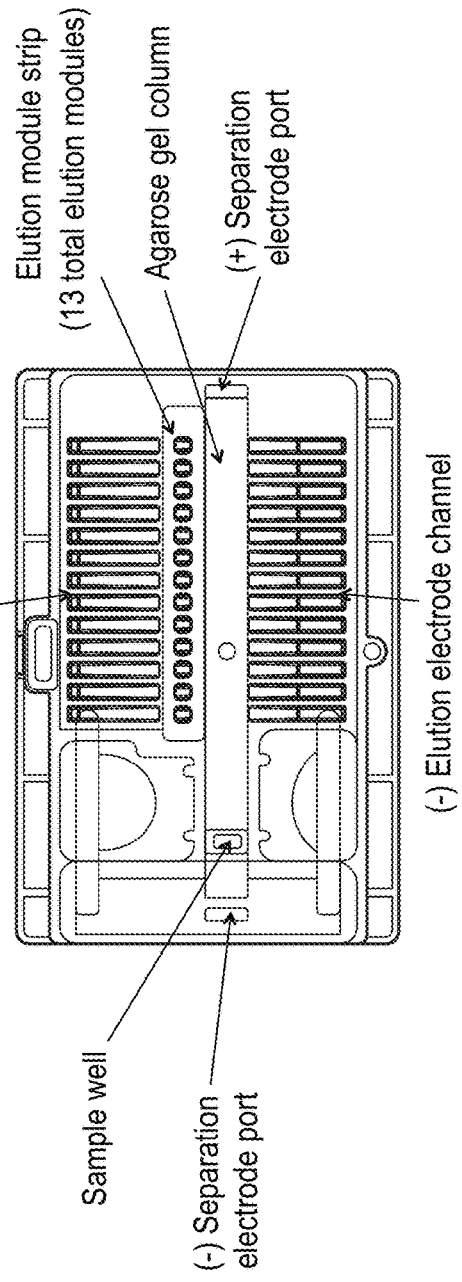
FIG. 5A shows a SageELF cassette for DNA size separation followed by electroelution, according to some embodiments.
Figure 5B:
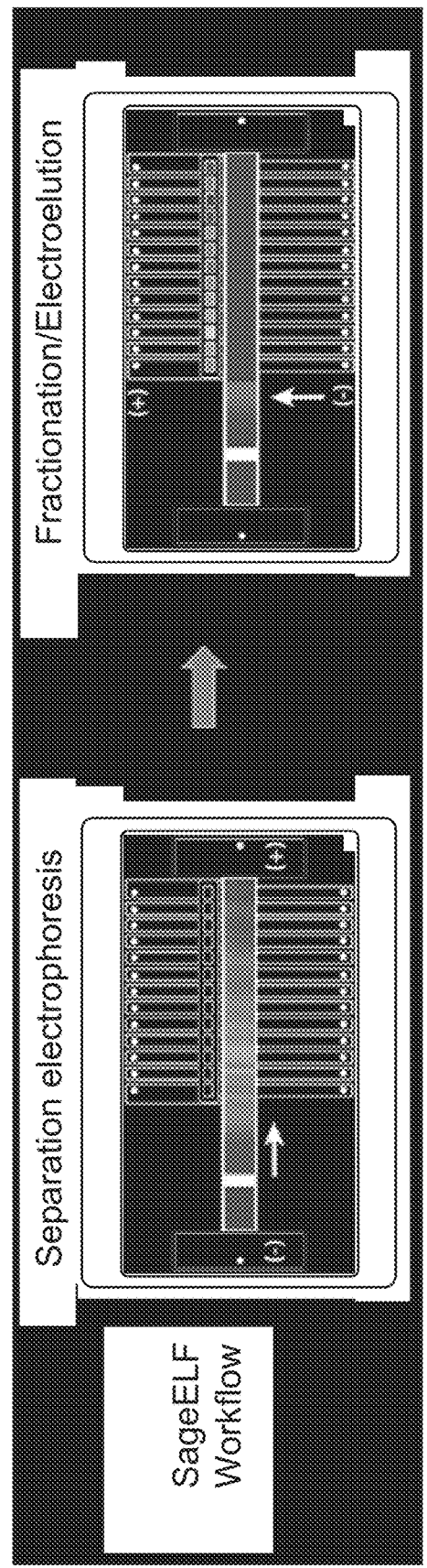
FIG. 5B shows an exemplary SageELF workflow from separation electrophoresis to fractionation/electroelution, according to some embodiments.

In some embodiments, the digested genomic DNA fragments are size-separated and electroeluted in electrophoresis cassettes shown in FIG. 5A, FIG. 5B, also described in U.S. Pat. No. 9,599,590 (which is incorporated herein by reference) or FIG. 6, also described in PCT Application No. PCT/US2015/055833 (which is incorporated herein by reference). After size fractionation, the entire DNA content of the separation gel is electroeluted laterally in to a contiguous series of elution modules arranged on one side of the separation gel column. The fractionated DNA is electroeluted into liquid electrophoresis buffer in the elution modules and can be directly added to PCR reactions and assayed for single-copy sequence targets within the excised repeat expansion fragment. Since the size of DNA in each elution fraction is determined by electrophoresis conditions (such as, for example, gel percentage, buffer, run time, voltage), the location of positive PCR signals within the elution fractions can be related directly to the size of the repeat region allele detected.

In some embodiments, the apparatuses, methods, and systems described in PCT/US2015/055833 are employed to accomplish all pre-PCR steps. Exemplary workflows are illustrated in schematic form in FIGS. 7A-10B. As described in PCT Application No. PCT/US2015/055833, high molecular weight genomic DNA may be extracted and digested in one integrated workflow with minimal user intervention. Specific cleavage to produce the detectable repeat expansion fragments can be accomplished with DNA restriction enzymes, such as traditional DNA restriction enzymes, (FIGS. 7A-7E and FIGS. 8A-8B), or with RNA-directed cleavases such as *Streptococcus pyogenes* Cas9 (FIGS. 9A-9E and FIGS. 10A-10B). Input materials such as purified white blood cells, unfractionated whole blood, and cell suspensions (or nuclei) obtained from dissociated tissue samples, can be used.

As shown in FIG. 1B and FIG. 1C, systems and methods disclosed herein are also useful for detection of insertion and inversion rearrangements. In both cases, the rearrangements change the distance between unique cleavage sites that flank one break point of the rearrangement (i.e., the insertion point, FIG. 1B, or one break point of the inversion, FIG. 1C).

As described in the Introduction, in some repeat expansion diseases, the expansions can be quite long and highly variable. To address this issue, electrophoresis conditions (including, for example, gel concentration, voltage, voltage waveform, buffer composition, run time) can be tailored so that all DNA molecules greater than a certain length will migrate together as a limiting low mobility fraction. This occurs when the increase in electrophoretic mobility caused by length (that is, increased charge from the phosphate backbone) is cancelled by the decrease in electrophoretic mobility caused by increased drag of the larger molecule. The size of molecules at this limiting low mobility point is a complex function of gel percentage, voltage, and buffer composition. However, for a given buffer and gel concentration, limiting low mobilities for DNA may be adjusted in agarose gels in the range of 1000 bp up to many 10,000 s of bp. FIGS. 11A-11B show electrophoresis conditions on the SageHLS cassette (as described in PCT/US2015/055833) where a limiting low mobility band beginning at 10,000 bp can be eluted in elution module number 2.

In some embodiments, electrophoresis conditions for a specific repeat expansion locus may be tailored so that unexpanded repeat fragments are eluted near the bottom of the gel column, moderately expanded repeat fragments will be resolved in fractions above the unexpanded fractions in the middle range of the elution fractions, and fragments with extremely large expansions will elute in the limiting low mobility compression band near the top of the gel column (FIGS. 8A-8B and FIGS. 10A-10B).

Example 1. Demonstration of SageHLS Workflow for Integrated Extraction, Cas9 Digestion, Electroelution, and qPCR Assay for a Specific Chromosomal Locus This example illustrates use of SageHLS to purify high molecular weight genomic DNA from an input cell samples, selectively excise the a specific 198 kb genomic DNA fragment from the BRCA1 locus using Cas9 cleavases, and finally, size-select and elute the BRCA1-containing fragment in one integrated workflow. The HLS elution fractions were then assayed for BRCA1 fragment by pPCR.

Buffer definitions:
Electrophoresis Buffer, also known as 0.5×KBB (51 mM Tris (base), 29 mM TAPS (acid), 0.1 mM EDTA (acid), pH 8.7)
FSE Buffer: 15% w/v Ficoll 400, 0.25×KBB buffer, 80 mg/mL sucrose, 10 mM EDTA
ERB Buffer: 0.5×KBB with addition of 32 mg/ml beta-cyclodextrin, 10 mM $MgCl_2$, 50 µg/ml BSA
HLS Lysis Buffer: 1×KBB, 2% glycerol, 3% SDS, 2.5 µg/ml bromophenol blue, 2.5 µg/ml phenol red Human cultured cells (Raji cell line) were washed several times by low speed centrifugation and resuspension in phosphate buffered saline. After the final wash, the cells were resuspended in FSE buffer at a concentration of 1.5× $10^6$ cells per 70 microliters. Two 70 microliter samples of the resuspended cells in FSE were loaded into each of two sample wells of a SageHLS cassette (0.75% agarose). The reagent wells of both lanes were emptied and refilled with HLS Lysis buffer (approximately 230 microliters) and electrophoresis was carried out at 30° C., 55 V, for 1 hour.

After the purification electrophoresis, the sample wells and reagent wells were emptied. The reagent wells were refilled with ERB buffer (without enzyme). In one of the two lanes, the sample wells were refilled with 80 ul of ERB containing 1 micromolar wt *S. pyogenes* Cas9 enzyme (New England Biolabs) that had been assembled with a equimolar mixture of 5 two part guide RNAs, each at 5 micromolar concentration. In the other lane, ERB without enzyme was loaded in the sample well as a mock digestion control. The sample well heater of the HLS instrument was adjusted to 37° C., and the Cas9 mixture was electrophoresed into the gel at 55V for 1 minute. After the 1 minute electrophoresis, the sample well was emptied and refilled with ERB buffer without enzyme. The cassette was incubated without electrophoresis for 30 minutes, with the sample well at 37° C., to allow Cas9 digestion of the purified DNA.

After digestion, the reagent wells were emptied and refilled with HLS lysis buffer, and size separation electrophoresis was carried out using a 4 hour pulsed field program designed to move the 200 kb BRCA1 digestion product to elution module 3 (Stage 3 program for HLS-CATCH 100-400 kb, SageHLS User Manual, Sage Science, Inc.). After size separation, electroelution was carried out using a continuous field voltage of 50 V for 1.5 hours.

Two-part guide RNAs were ordered from IDT (ALT-R™ crRNA and tracRNA). The gRNAs were chosen to excise a 198 kb fragment that includes the entire BRCA1 locus with ample flanking sequence on 5' and 3' sides (see FIG. 12).

Figure 12:
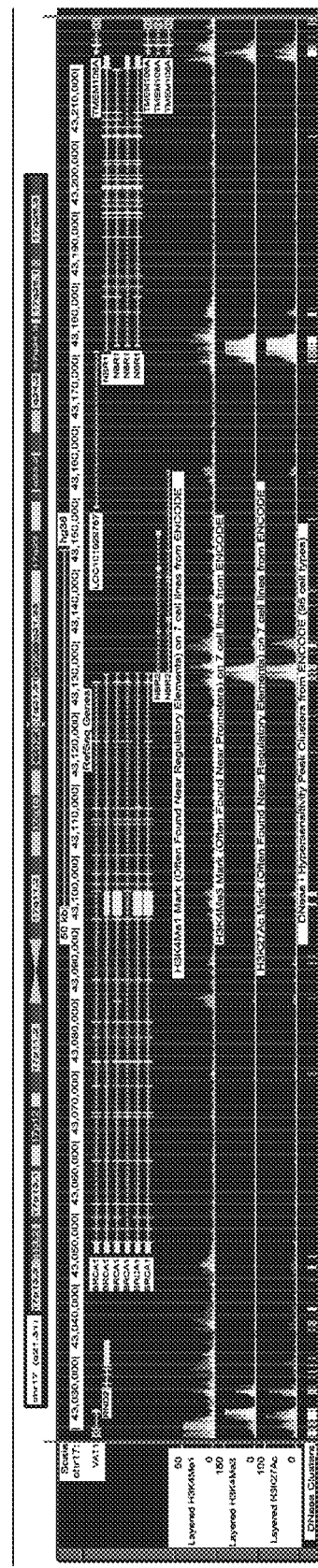
FIG. 12 shows an exemplary schematic diagram, according to some embodiments.

Three crRNAs were designed for the right side of the gene—BRCA1gR67:GCTTATTACATTCTCGGCCA (SEQ ID NO: 1); BRCA1gR68: CTTATTACATTCTCGGCCAT (SEQ ID NO: 2); and BRCA1gR69: ATTACATTCTCGGCCATGGG (SEQ ID NO: 3). Two crRNAs were designed for the left side of the gene—BRCA1gLL1: CCTCTGGGAGCCACAGGCCA (SEQ ID NO: 4); and BRCA1gLL3: GCCATGACAACAACCCAGAC (SEQ ID NO: 5) (FIG. 12). The crRNAs and tracRNA (IDT) were dissolved in IDT duplexing buffer and annealed by incubating a mixture containing 50 micromolar tracRNA and 10 micromolar of each of the 5 crRNAs (total 50 micromolar in crRNAs) for 5 minutes at 95° C. and 15 minutes of cooling at ambient lab temperature on the benchtop. Annealed gRNA and Cas9 enzyme were assembled by assembling the final reaction mixture in ERB buffer (see above) and incubating the mix at 37° C. for 10 minutes prior to addition to the HLS cassette.

Figure 13A:
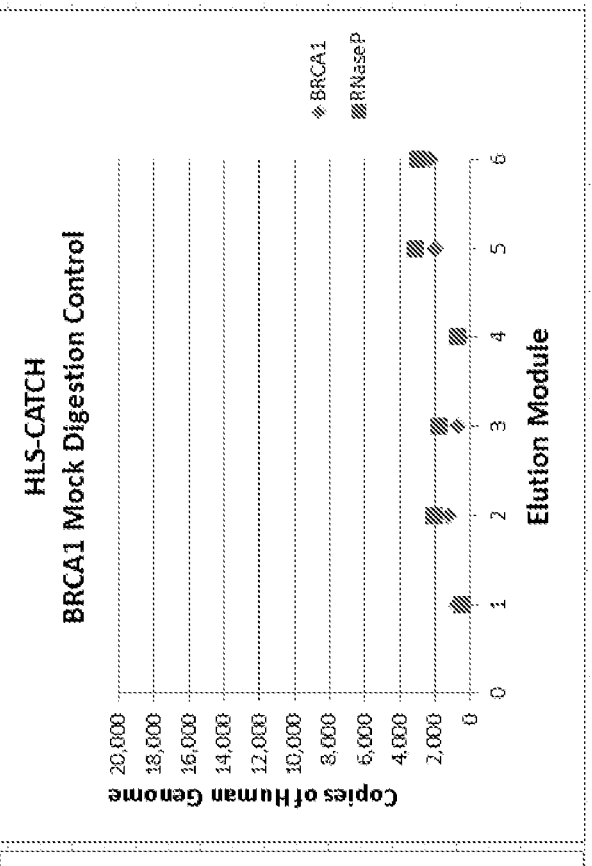
FIGS. 13A-13B shows graphs of results achieved in Example 1, according to some embodiments.
Figure 13B:
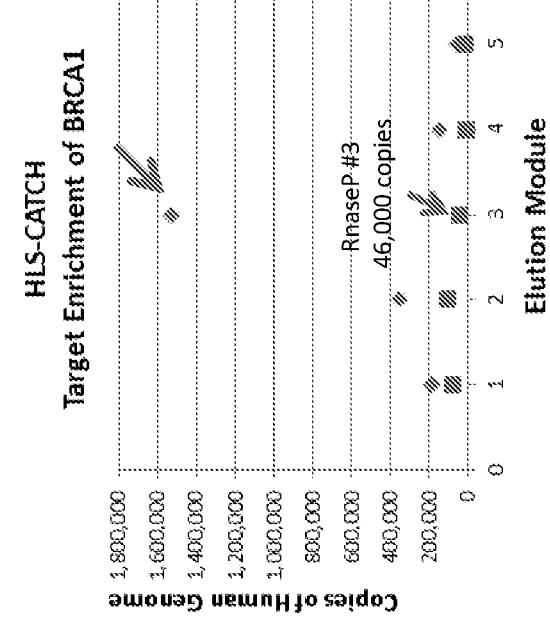

After elution, eluted products were diluted 1:10 in 10 mM Tris-HCl, 1 mM EDTA, pH 8.0, and assayed by Taqman qPCR for BRCA1 gene DNA, using the RNaseP RNA gene as a reference locus for the non-target DNA. (ABI/Life Technologies part numbers:#4400291—BRCA1 copy number assay (Hs00300666-cn amplicon, small); #4403326—RNaseP copy number reference assay; #4371355—Taqman GT Master Mix; qPCR instrument; ABI QuantStudio 3). The results in FIGS. 13A-13B show recovery of $1.5 \times 10^6$ copies of the BRCA1 fragment were recovered in fraction 3 of the Cas9-digested cassette lane, but only background signals were seen in the mock-digested cassette lane.

Example 2. Demonstration of Gel Compression Useful for Detection of High Molecular Structural Variants Samples of DNA markers (1 kb Extend marker, New England Biolabs) was loaded into sample well of two lanes of a SageHLS cassette. The DNA was separated and electroeluted in using the following electrophoresis conditions: 0.75% agarose, 50 mM Tris, 29 mM TAPS, 0.1 mM EDTA, pH 8.7, 55 V continuous field (DC), 50 minutes, gel temperature 30° C. Electroeluted fractions from all elution wells were analyzed on an analytical agarose slab gel (FIGS. 11A-11B). Evidence of electrophoretic mobility compression in the HLS separation run is seen in Fraction #2 (that is, fragments 10-48.5 kb comigrate and are found together in fraction #2, and no DNA is found in Fraction #1). Therefore, due to the compression phenomenon, under these conditions, all DNA greater than 10 kb will be found in fraction #2. Fractions #5 and #6 contain fragments ranging from 1-2 kb.

REFERENCES

La Spada A. R. and Taylor, J. P., Repeat expansion disease: progress and puzzles in disease pathogenesis. Nature Reviews Genetics 11:247-258.

Nolin S. L., et al., Expansion of the Fragile X CGG Repeat in Females with Premutation or Intermediate Alleles. Am. J. Hum. Genet. 72:454-464, 2003.

| 6-50 unaffected | 18-150 bp |
| 60-200 "premutation" | 180-600 bp |
| Full mutation > 200 | >600 bp |

Suh, E. R., et al., Semi-automated quantification of C9orf72 expansion size reveals inverse correlation between hexanucleotide repeat number and disease duration in frontotemporal degeneration. Acta Neuropathol 130(3): 363-372, 2015.

Unaffected 2-8 (12-48 bp) affected 300-3800 (1800-22800 bp)

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to molecular processing. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference/prior art by specifically lacking one or more elements/features of a system, device and/or method disclosed in such prior art. In other words, claims to certain embodiments may contain negative limitation to specifically exclude one or more elements/features resulting in embodiments which are patentably distinct from the prior art which include such features/elements.

The invention claimed is:

1. A method, comprising:
providing an electrophoresis cassette comprising:
at least one sample well,
at least one gel column containing a separation gel, and
an elution module array comprising a plurality of elution modules arranged adjacent the at least one gel column;
isolating high-molecular weight (HMW) DNA from a sample;
enzymatically cleaving the HMW DNA isolated from the sample within single-copy DNA sequences on both sides of a genomic DNA region that contains a simple sequence repeat region ("region") to produce a cleaved sample;
fractionating the cleaved sample by gel electrophoresis through the separation gel;
electroeluting the fractionated DNA from the separation gel into the plurality of elution modules arranged adjacent to the at least one gel column, thereby creating a plurality of size fractions from the cleaved sample;
subjecting the size fractions to qPCR assays to detect single-copy sequences within the genomic fragments that also carry the region;
determining the length of a size of the size fractions showing a positive qPCR signal from their position within the elution module array;
and
determining the length of the region in the size fractions showing a positive qPCR signal and the known positions of the enzymatic cleavage sites.

2. The method of claim 1, wherein the cleaving is performed by restriction enzymes.

3. The method of claim 2, wherein the restriction enzymes are chosen not to cut within the region.

4. The method of claim 1, wherein the length of the region can be correlated with the presence or absence of a genetic condition or disease.

5. The method of claim 1, wherein the cleaving is performed with one or more RNA- or DNA-directed cleavase.

6. The method of claim 5, wherein the RNA- or DNA-directed cleavase is one or more of: Cas9, Cpf1, and NgAgo.

7. The method of claim 5, wherein the enzymatic cleavage sites lie outside of the region.

* * * * *